(12) United States Patent
Nabutovsky et al.

(10) Patent No.: US 9,462,959 B2
(45) Date of Patent: Oct. 11, 2016

(54) METHODS AND SYSTEMS THAT USE IMPLANTED POSTURE SENSOR TO MONITOR LEFT ATRIAL PRESSURE AND/OR INTER-THORACIC FLUID VOLUME

(75) Inventors: Yelena Nabutovsky, Sunnyvale, CA (US); Fujian Qu, Sunnyvale, CA (US); Steve Koh, S. Pasadena, CA (US); Dan E. Gutfinger, Agoura Hills, CA (US); Alex Soriano, Ventura, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1557 days.

(21) Appl. No.: 12/649,665

(22) Filed: Dec. 30, 2009

(65) Prior Publication Data

US 2011/0125207 A1    May 26, 2011

Related U.S. Application Data

(60) Provisional application No. 61/263,270, filed on Nov. 20, 2009.

(51) Int. Cl.
| | |
|---|---|
| *A61N 1/00* | (2006.01) |
| *A61B 5/053* | (2006.01) |
| *A61B 5/021* | (2006.01) |
| *A61B 5/11* | (2006.01) |
| *A61B 5/00* | (2006.01) |
| *A61N 1/362* | (2006.01) |
| *A61N 1/365* | (2006.01) |
| *A61N 1/372* | (2006.01) |
| *A61N 1/368* | (2006.01) |

(Continued)

(52) U.S. Cl.
CPC ............... *A61B 5/053* (2013.01); *A61B 5/021* (2013.01); *A61B 5/1116* (2013.01); *A61B 5/4878* (2013.01); *A61N 1/3627* (2013.01); *A61N 1/36521* (2013.01); *A61N 1/36564* (2013.01); *A61N 1/36585* (2013.01); *A61N 1/37258* (2013.01); *A61B 5/686* (2013.01); *A61B 5/7275* (2013.01); *A61N 1/3684* (2013.01); *A61N 1/3702* (2013.01); *A61N 1/3962* (2013.01)

(58) Field of Classification Search
CPC ..................... A61B 5/1116; A61N 1/36521
USPC ....... 607/5, 6, 17, 30, 62; 600/481, 529, 544, 600/546
See application file for complete search history.

(56) References Cited

U.S. PATENT DOCUMENTS

| | | |
|---|---|---|
| 5,003,976 A | 4/1991 | Alt |
| 6,970,742 B2 | 11/2005 | Mann |

(Continued)

FOREIGN PATENT DOCUMENTS

WO        2006023786        3/2006

*Primary Examiner* — William Levicky
*Assistant Examiner* — Lindsey G Hankins
(74) *Attorney, Agent, or Firm* — Theresa A. Raymer

(57) ABSTRACT

In specific embodiments, a method to monitor left atrial pressure and/or intra-thoracic fluid volume of a patient, comprises (a) monitoring posture of the patient using a posture sensor implanted within the patient, and (b) using portions of an impedance signal, obtained using implanted electrodes, to monitor the left atrial pressure and/or intra-thoracic fluid volume of the patient. Each portion of the impedance signal used to monitor the left atrial pressure and/or intra-thoracic fluid volume of the patient corresponds to a period after which the patient has maintained a predetermined posture for at least a predetermined period of time, and during which the patient has remained in the predetermined posture.

18 Claims, 14 Drawing Sheets

(51) Int. Cl.
 *A61N 1/37* (2006.01)
 *A61N 1/39* (2006.01)

(56) References Cited

U.S. PATENT DOCUMENTS

| | | |
|---|---|---|
| 7,335,161 B2 | 2/2008 | Von Arx |
| 7,794,404 B1* | 9/2010 | Gutfinger ............... A61B 5/021 600/486 |
| 2002/0002389 A1* | 1/2002 | Bradley ............. A61N 1/36521 607/8 |
| 2004/0077995 A1* | 4/2004 | Ferek-Petric et al. .......... 604/66 |
| 2006/0041281 A1 | 2/2006 | Von Arx |
| 2006/0241513 A1* | 10/2006 | Hatlestad ............. A61B 5/0809 600/547 |
| 2008/0091114 A1* | 4/2008 | Min et al. ..................... 600/508 |
| 2008/0132967 A1 | 6/2008 | Von Arx |
| 2008/0195165 A1 | 8/2008 | Stahmann |
| 2010/0010583 A1* | 1/2010 | Panken et al. ................. 607/62 |
| 2010/0211135 A1* | 8/2010 | Caparso et al. ............... 607/62 |

\* cited by examiner supine prone

METHODS AND SYSTEMS THAT USE IMPLANTED POSTURE SENSOR TO MONITOR LEFT ATRIAL PRESSURE AND/OR INTER-THORACIC FLUID VOLUME

PRIORITY CLAIM

This application claims priority to U.S. Provisional Patent Application No. 61/263,270, entitled "Use of Posture Sensor to Increase Accuracy of Implantable Sensor" filed Nov. 20, 2009.

CROSS-REFERENCE TO RELATED APPLICATIONS

This application is related to the following commonly assigned U.S. Patent Applications, each of which is incorporated herein by reference: U.S. patent application Ser. No. 11/863,516, entitled "Use of Cardiogenic Impedance Waveform Morphology to Analyze Cardiac Conditions and to Adjust Treatment Therapy" (Nabutovsky et al), filed Sep. 28, 2007, which is incorporated herein by reference; and U.S. patent application Ser. No. 12/649,647, entitled "Methods and Systems that Use Implanted Posture Sensor to Monitor Pulmonary Edema," filed the same day as the present application.

FIELD OF THE INVENTION

Embodiments of the present invention relate to systems and methods for increasing accuracy of left atrial pressure (LAP) and/or intra-thoracic fluid volume estimated by measuring impedance between two or more electrodes.

BACKGROUND

Heart failure (HF) decompensation is characterized by increased left atrial pressure (LAP) causing symptomatic pulmonary congestion and edema. There may be multiple different catalysts for acute HF, but a common aggravating condition is elevated LAP. The rise in LAP usually is gradual and precedes symptom onset. Accurate monitoring of LAP can enable early diagnosis of incipient decompensation and guide treatment. There are at least three techniques for measuring or estimating LAP. A first technique is direct measurement of LAP using an implantable sensor positioned in the left atrium, as taught in U.S. Pat. No. 6,970,742, entitled, "Method for Detecting, Diagnosing, and Treating Cardiovascular Disease" (Mann et al.), which is incorporated herein by reference. A second technique, widely used in clinical practice, is an estimation of LAP using pulmonary capillary wedge pressure measured by a fluid-filled catheter. A third technique is an indirect estimation of LAP based on estimated intra-thoracic fluid volume changes. This technique relies on the fact that LAP is the primary force governing fluid filtration between the intravascular space and the extravascular space including interstitial space, pulmonary alveolar space, and plural space.

In the third technique described above, LAP is estimated by measuring impedance (Z) between two or more implanted electrodes, for example two or more implantable cardioverter-defibrillator (ICD) or cardiac resynchronization therapy defibrillator (CRT-D) lead electrodes. LAP estimation based on impedance measurements (referred to herein as zLAP) taken between two or more electrodes implanted within the heart is described in U.S. Pat. No. 5,003,976, entitled, "Cardiac and pulmonary physiological analysis via intracardiac measurements with a single sensor" (Alt), which patent document is incorporated herein by reference. Measurement of impedance need not require additional invasive procedures and can potentially offer non-invasive measurements of LAP when a device, such as an ICD or CRT-D, is already implanted. However, impedance measurements are susceptible to drift and/or imprecision due to factors unrelated to LAP, and therefore monitoring based solely on impedance derived LAP may not produce satisfactory results for use in diagnosis and/or treatment. It can be useful to improve the accuracy of zLAP as an estimate for directly measured LAP.

One condition that can result from a failing heart is pulmonary edema. Pulmonary edema is the fluid accumulation in the lungs that may result from elevated LAP over a period of time. Pulmonary edema leads to impaired gas exchange and may cause respiratory failure, and if left untreated can lead to coma and even death due to its main complication of hypoxia. Pulmonary edema may be suspected in the presence of cardiovascular disease and confirmed through physical examination and chest x-ray. In addition, blood tests are typically performed for electrolytes and markers of renal function in order to select an appropriate method of treatment. Usually, by the time a patient presents to the hospital with suspected pulmonary edema, he or she is experiencing symptoms such as shortness of breath with minimal exertion, orthopnea, and swelling of extremities. Prolonging time to treatment increases risk of complications. In addition, a physician examination is subjective and depends on the level of skill and experience of the physician as well as clarity of symptoms. Therefore, it is desirable to improve the timeliness and accuracy of diagnosis to potentially reduce damage caused by such conditions.

SUMMARY

Embodiments of the present invention are related to implantable systems, and methods for use therewith for monitoring LAP, LAP surrogates, and/or intra-thoracic fluid volume of a patient. In accordance with an embodiment, a posture sensor is used with an implantable device having or connected to at least two electrodes between which is obtained an impedance signal. Data indicative of the impedance signal and a corresponding posture of the patient is stored. One or more snapshots of the impedance signal are identified from the stored data where the patient has maintained a predetermined posture prior to each snapshot for at least a first specified period of time and where the patient maintains the predetermined posture for at least a second specified period of time. One or both of the posture sensor and the implantable device can be subcutaneously implanted, or intra-thoracically implanted, but is not limited thereto. In some embodiments, the implantable device can be an implantable cardioverter-defibrillator (ICD) and/or pacemaker and impedance can be obtained in part by one or more of the electrodes connected with the left and/or right ventricular leads. The impedance signal is used to determine zLAP, which is monitored for one or more of detecting abnormalities in LAP, detecting efficacy of treatment, and adjusting pacing parameters of the pacemaker. When any of the monitored-for conditions satisfy predetermined criteria, a response can be triggered.

In an alternative embodiment, a posture sensor is used with an implantable device having or connected to at least two electrodes to obtain portions of an impedance signal to monitor the left atrial pressure and/or intra-thoracic fluid volume of the patient. The selected portions of the impedance signal correspond to periods of time during which the patient has maintained a predetermined posture for at least a predetermined period of time. The impedance signal is used to determine left atrial pressure (LAP), which is monitored for one or more of detecting abnormalities in LAP, detecting efficacy of treatment, and adjusting pacing parameters of the pacemaker. When any of the monitored-for conditions satisfy predetermined criteria, a response can be triggered.

Further embodiments of the present invention are related to implantable systems, and method for use therewith for monitoring pulmonary edema of a patient. In accordance with an embodiment, a posture sensor is used with an implantable device having or connected to at least two electrodes to determine an amount of time it takes an impedance signal to achieve a steady state after the posture of the patient changes from a first predetermined posture to a second predetermined posture, where the impedance signal is obtained using the electrodes and is indicative of LAP and/or intra-thoracic fluid volume of the patient. Pulmonary edema of the patient is monitored based on the determined amount of time it takes the impedance signal to achieve the steady state after the posture of the patient changes from the first predetermined posture to the second predetermined posture. When pulmonary edema is detected, for example when a shift in the amount of time required to achieve steady state between two periods of measurement exceeds a threshold, a response can be triggered.

This description is not intended to be a complete description of, or limit the scope of, the invention. Other features, aspects, and objects of the various embodiments of the present invention can be obtained from a review of the specification, the figures, and the claims.

DETAILED DESCRIPTION

Figure 1:
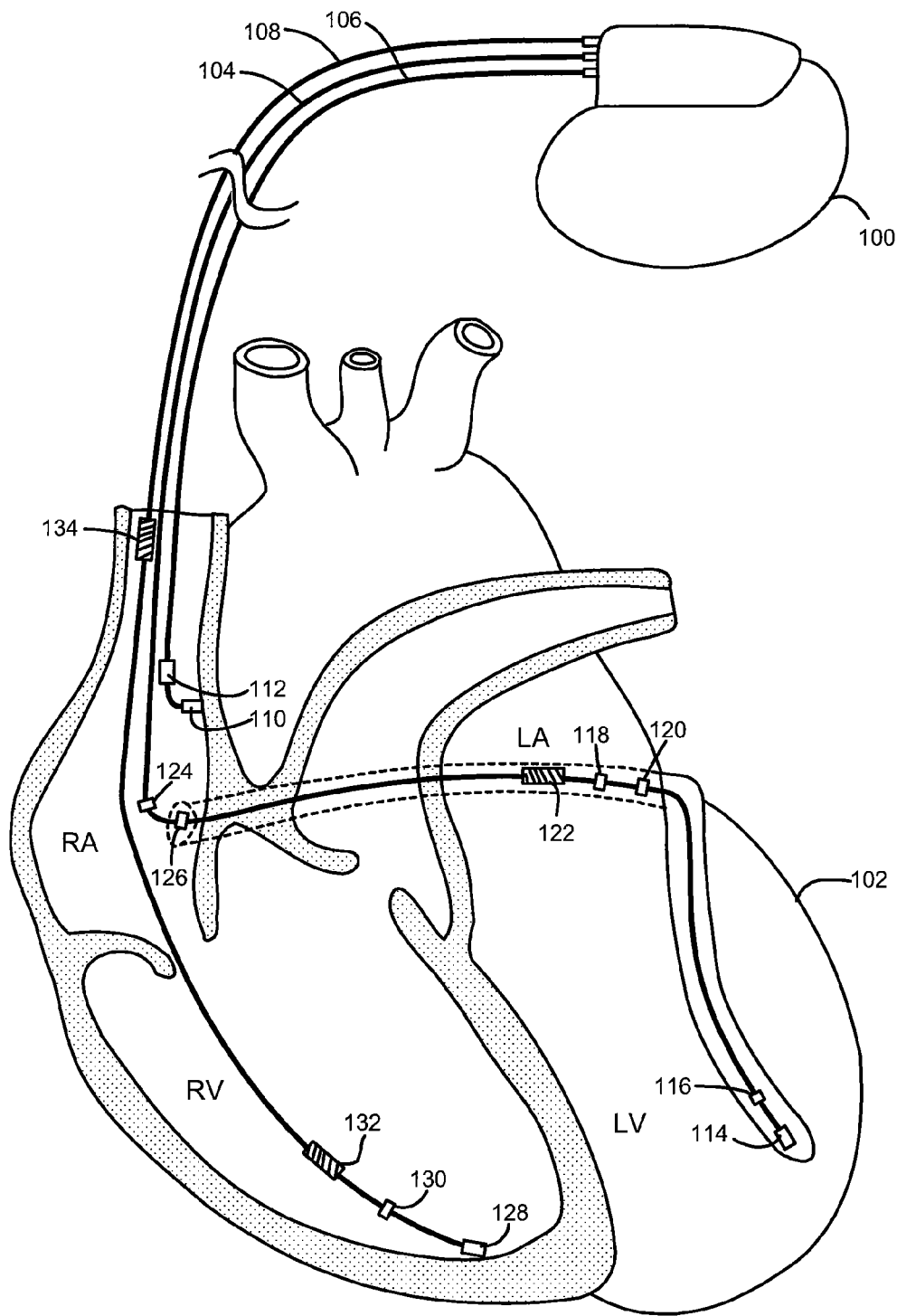
FIG. 1 is a diagram of an exemplary implantable device in relation to a human heart, including leads with electrodes that provide sensing vectors for obtaining cardiogenic impedance waveforms.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

The disclosed systems and methods of the present invention generally relate to systems and methods for using a posture sensor to improve and/or qualify zLAP calculations to estimate direct measured LAP. The disclosed systems and methods of the present invention also relate to systems and methods for using a posture sensor to determine cardiac conditions, such as an onset of pulmonary edema, and/or to adjust treatment therapy. The present invention relies on zLAP calculated based on impedance measurements obtained using two or more electrodes. While it is possible and within the scope of the present invention to employ one or more portions of the techniques of the present invention in an external (i.e., non-implantable) system or a subcutaneously implantable system, embodiments of the present invention are especially useful when employed by a cardiac device implanted within a patient for cardiac treatment, for example such as an ICD or CRT-D. Accordingly, an exemplary implantable cardiac device in which embodiments of the present invention are useful is first described with reference to FIGS. 1 and 2.

Exemplary Implantable Device

As shown in FIG. 1, an exemplary implantable medical device ("implantable device" 100), in this case an exemplary implantable cardioverter-defibrillator (ICD), is in electrical communication with a patient's heart 102 by way of three leads, 104, 106 and 108, suitable for sensing, delivering multi-chamber stimulation and shock therapy. Not every configuration has all of the illustrated electrodes, but a given actual configuration may include some of the illustrated electrodes and/or even more electrodes than illustrated.

To sense atrial cardiac signals and to provide right atrial chamber stimulation therapy, the implantable device 100 is coupled to an implantable right atrial lead 106, typically having an atrial tip electrode 110 and an atrial ring electrode 112, which typically is implanted in the patient's right atrial appendage. Implantable device 100 is also known as and referred to as a pacing device, a pacing apparatus, a cardiac rhythm management device, or an implantable cardiac stimulation device. Alternatively, the implantable device 100 could be a defibrillator, or cardioverter, or have combined pacing and defibrillation/cardioversion capabilities.

To sense left atrial and ventricular cardiac signals and to provide left chamber pacing therapy, the implantable device 100 is coupled to a "coronary sinus" lead 104 designed for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 104 is designed to receive atrial and ventricular cardiac signals and to deliver left ventricular pacing therapy using a left ventricular (LV) tip electrode 114 and a LV ring electrode 116. Left atrial pacing therapy uses, for example, first and second left atrial (LA) ring electrodes 118 and 120. Shocking therapy can be performed using at least a left atrial (LA) coil electrode 122. For a description of an exemplary coronary sinus lead, see U.S. Pat. No. 7,313,444, entitled, "Self-Anchoring Coronary Sinus Lead" (Pianca et al.), and U.S. Pat. No. 5,466,254, entitled, "Coronary Sinus Lead with Atrial Sensing Capability" (Helland), which patent documents are incorporated herein by reference. Coronary sinus lead 104 may also include a pair of right atrial (RA) ring electrodes 124 and 126, which may be used to provide right atrial chamber pacing therapy.

The implantable device 100 is also shown in electrical communication with the patient's heart 102 by way of an implantable right ventricular lead 108, typically having a right ventricular (RV) tip electrode 128, an RV ring electrode 130, an RV coil electrode 132, and a superior vena cava (SVC) coil electrode 134 (also known as a right atrial (RA) coil electrode). Typically, the right ventricular lead 108 is transvenously inserted into the heart 102 so as to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Impedance measurements can be obtained using a single vector, or using multiple vectors simultaneously, quasi-simultaneously, or sequentially using any of the electrodes illustrated in FIG. 1, either in pairs or in combinations of three or more electrodes. For example, a multi-vector network that includes three intracardiac vectors: a vector between the left ventricle (LV) and the right atrium (RA), a vector between the LV and the right ventricle (RV), and a vector between two electrodes in the right ventricle (RV), can be used to obtain an impedance signal. It is noted that the case 100 of the implantable device can also be used as an electrode. The term multi-vector network as used herein refers to any multi-vector network with two or more vectors between physical, logical, and or virtual electrodes, such as between the physical electrodes illustrated in FIG. 1. A single vector used to obtain an impedance signal can include as few as two electrodes, e.g., a LV ring electrode and a RV ring electrode. These are just a few examples, which are not meant to be limiting.

Figure 2:
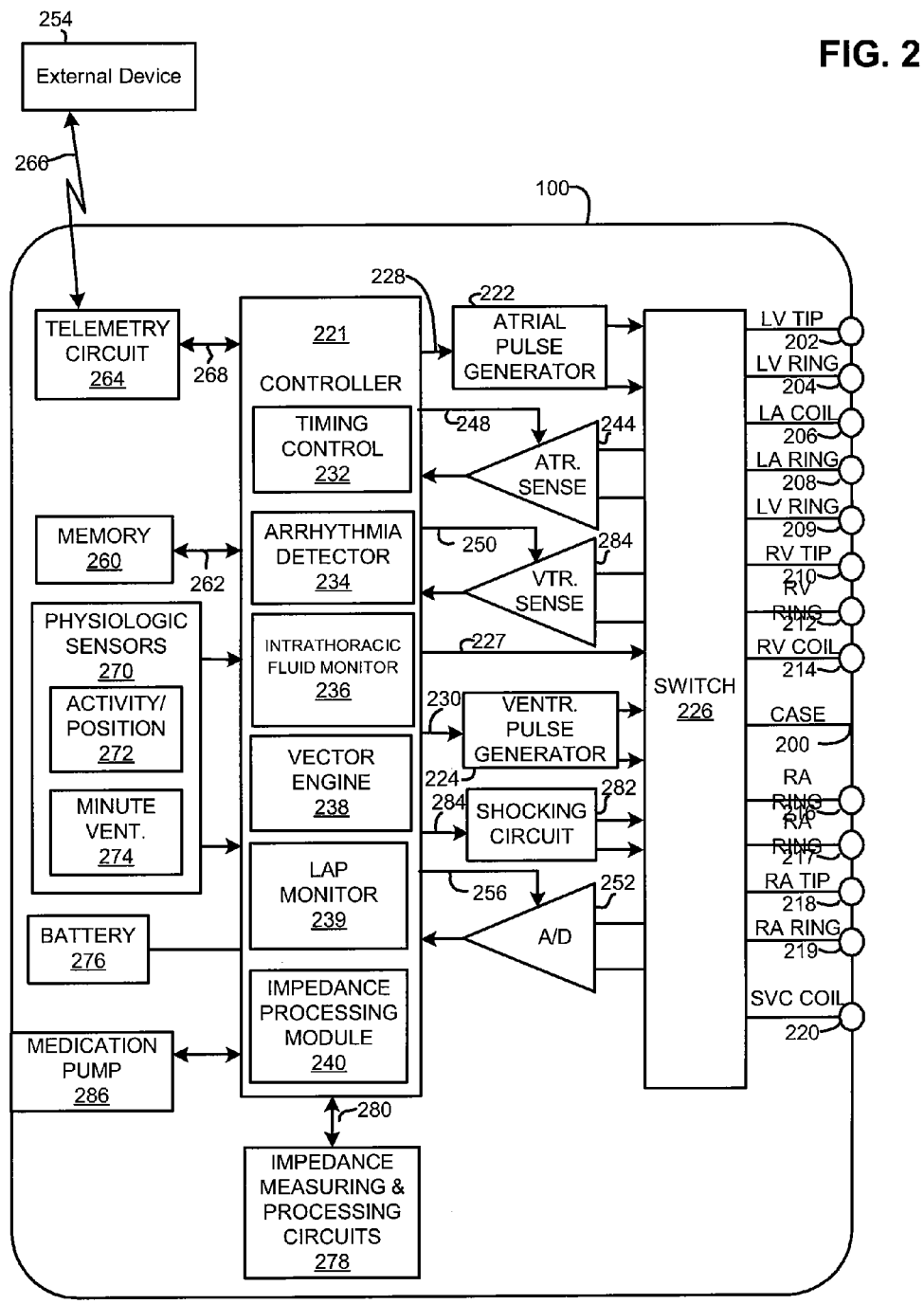
FIG. 2 is a high level block diagram of the exemplary implantable device of FIG. 1, in greater detail.

FIG. 2 shows an exemplary block diagram depicting various components of the exemplary implantable device 100. The components are typically contained in a case 200, which is often referred to as the "can", "housing", "encasing", or "case electrode", and may be programmably selected to act as the return electrode for unipolar operational modes. The case 200 may further be used as a return electrode alone or in combination with one or more of the coil electrodes 122, 132, 134 for stimulating purposes. The case 200 further includes a connector (not shown) having a plurality of terminals (202, 204, 206, 208, 209, 210, 212, 214, 216, 217, 218, 219, and 220—shown schematically with the names of the electrodes to which they are connected shown next to the terminals), including: a left ventricular tip terminal (LV TIP) 202 for left ventricular tip electrode 114; a left ventricular ring terminal (LV RING) 204 for left ventricular ring electrode 116; a left atrial shocking terminal (LA COIL) 206 for left atrial coil electrode 122; a left atrial ring terminal (LA RING) 208 for left atrial ring electrode 118; a left atrial ring terminal (LA RING) 209 for left atrial ring electrode 120; a right ventricular tip terminal (RV TIP) 210 for right ventricular tip electrode 128; a right ventricular ring terminal (RV RING) 212 for right ventricular ring electrode 130; a right ventricular shocking terminal (RV COIL) 214 for RV coil electrode 132; a right atrial ring terminal (RA RING) 216 for atrial ring electrode 124; a right atrial ring terminal (RA RING) 217 for right atrial ring electrode 126; a right atrial tip terminal (RA TIP) 218 for atrial tip electrode 110; a right atrial ring terminal (RA RING) 219 for atrial ring electrode 112; and a SVC shocking terminal (SVC COIL) 220 for right atrial SVC coil electrode 134.

The exemplary implantable device 100 may include a programmable microcontroller 221 that controls various operations of the implantable device 100, including cardiovascular monitoring, hemodynamic monitoring, and cardiovascular stimulation therapy. Microcontroller 221 includes a microprocessor (or equivalent control circuitry), RAM and/or ROM memory, logic and timing circuitry, state machine circuitry, and I/O circuitry.

The exemplary implantable device 100 may further include an atrial pulse generator 222 and a ventricular pulse generator 224 that generate pacing stimulation pulses for delivery by the right atrial lead 106, the coronary sinus lead 104, and/or the right ventricular lead 108 via an electrode configuration switch 226. The electrode configuration switch 226 may include multiple switches for connecting the desired electrodes to the appropriate I/O circuits, thereby providing complete electrode programmability. Accordingly, switch 226, in response to a control signal 227 from the microcontroller 221, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 221 via appropriate control signals 228 and 230, respectively, to trigger or inhibit the stimulation pulses.

Microcontroller 221 is illustrated as including timing control circuitry 232 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 221 may also implement an arrhythmia detector 234, a vector engine 238, and an impedance processing module 240. The microcontroller 221 may process input from physiological sensors 270, such as accelerometers of an activity/position module 272, and a minute ventilation module 274, etc. The arrhythmia detector 234 can detect arrhythmias based on obtained IEGMs and/or cardiogenic impedance signals, in accordance with embodiments of the present invention. For example, the arrhythmia detector can detect arrhythmias and/or discriminate between arrhythmias, based on the morphology of cardiogenic impedance signals, using embodiments of the present invention described below. The microcontroller 221 can also implement a LAP monitor 239, which can monitor LAP as described more fully below, and an intrathoracic fluid monitor 236 to monitor for conditions such as pulmonary edema, in accordance with embodiments of the present invention described below.

The components 232, 234, 236, 238, 239 and 240 may be implemented in hardware as part of the microcontroller 221, or as software/firmware instructions programmed into an implementation of the implantable device 100 and executed on the microcontroller 221 during certain modes of operation. Although not shown, the microcontroller 221 may further include other dedicated circuitry and/or firmware/software components that assist in monitoring various conditions of the patient's heart and managing pacing therapies. It also possible that part of, or entire components 232, 234, 236, 238, 239 and 240 can be implemented external to the microcontroller 221, e.g., using dedicated circuitry and/or firmware/software components within the implantable device 100, and/or within an external device (e.g., 254).

Atrial sensing circuits 244 and ventricular sensing circuits 246 may also be selectively coupled to the right atrial lead 306, coronary sinus lead 304, and the right ventricular lead 308, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power precision amplifiers with programmable gain and/or automatic gain control, bandpass filtering, and a threshold detection circuit to selectively sense the cardiac signal of interest. The automatic gain control enables the exemplary implantable device 100 to sense low amplitude signal characteristics of atrial or ventricular fibrillation.

The outputs of the atrial and ventricular sensing circuits 244 and 246 are connected to the microcontroller 221 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 221 over signal lines 248 and 250 to control, for example, the gain and the timing of blocking circuitry (not shown) optionally coupled to the inputs of the sensing circuits 244, 246.

Cardiac signals, including signals involved in impedance measurements, can be supplied to an analog-to-digital (A/D) data acquisition system 252, which is configured to acquire these signals, convert the raw analog data into a digital signal, and store the digital signals for later processing and/or telemetric transmission to an external device 254. The data acquisition system 252 is coupled to the right atrial lead 306, the coronary sinus lead 304, and the right ventricular lead 308 through the switch 226 to process signals across any pair of desired electrodes.

The data acquisition system 252 is coupled to the microcontroller 221, or other detection circuitry, to assist in detecting an evoked response from the heart 102 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 221 detects a depolarization signal during a window following a stimulation pulse, the presence of which indicates that capture has occurred. The microcontroller 221 enables capture detection by triggering the ventricular pulse generator 224 to generate a stimulation pulse, starting a capture detection window using the timing control circuitry 232 within the microcontroller 221, and enabling the data acquisition system 252 via control signal 256 to sample the cardiac signal that falls in the capture detection window and, based on the amplitude, determines if capture has occurred.

The microcontroller 221 is further coupled to a memory 260 by a suitable data/address bus 262. The programmable operating parameters used by the microcontroller 221 are stored in memory 260 and used to customize the operation of the exemplary implantable device 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 102 within each respective tier of therapy. The memory 260 can also store impedance signal data, posture data, zLAP data, and/or pulmonary edema related data, in accordance with embodiments of the present invention discussed below.

The operating parameters of the exemplary implantable device 100 may be non-invasively programmed into the memory 260 through a telemetry circuit 264 in telemetric communication via communication link 266 with the external device 254, such as a programmer, local transceiver, or a diagnostic system analyzer. The microcontroller 221 can activate the telemetry circuit 264 with a control signal 268. The telemetry circuit 264 allows intracardiac electrograms, cardiogenic impedance signals and status information relating to the operation of the exemplary implantable device 100 (as contained in the microcontroller 221 or memory 260) to be sent to the external device 254 through an established communication link 266.

The physiological sensors 270 referred to above can further include, for example, "rate-responsive" sensors that adjust pacing stimulation rates according to the exercise state of the patient. Accordingly, the microcontroller 221 responds by adjusting the various pacing parameters (such as rate, etc.) at which the atrial and ventricular pulse generators 222 and 224 generate stimulation pulses.

The physiological sensors 270 may include mechanisms and sensors to detect bodily movement 272, minute ventilation 274, changes in blood pressure, changes in cardiac output, changes in the physiological condition of the heart, diurnal changes in activity (e.g., detecting sleep and wake states), G-force acceleration of the ICD case 200, length of the cardiac QT interval, blood oxygen saturation, blood pH, changes in temperature, respiration rate, and QRS wave duration. While shown as being included within the exemplary implantable device 100, the physiological sensor(s) 270 may also be external to the exemplary implantable device 100, yet still be implanted within or carried by the patient, e.g., a blood pressure probe. Examples of physiological sensors external to the case 200 that may be deployed by implantable device 100 include sensors that, for example, sense respiration activities, O2 saturation, evoked response, pH of blood, and so forth.

The illustrated physiological sensors 270 include one or more activity/position sensors 272 (e.g., 1D or 3D accelerometers, movement sensors, etc.) to detect changes in the patient's position, at least one of the activity/position sensors 272 being a posture sensor comprising a 3D accelerometer. The activity/position sensors 272 can be used to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up). As described in detail below, the posture sensor of the one or more activity/position sensors 272 can be used to improve and/or qualify zLAP calculations to estimate direct measured LAP and/or to monitor cardiac conditions, such as an onset of pulmonary edema, and/or to adjust treatment therapy.

In one configuration, an accelerometer output signal is bandpass-filtered, rectified, and integrated at regular timed intervals. Such a processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

The minute ventilation (MV) sensor 274 may also be included in the physiological sensors 270 in order to sense rate and depth of breathing. Minute ventilation can be measured as the total volume of air that moves in and out of a patient's lungs in a minute. The MV sensor 274 may use impedance measuring and processing circuits 278 to sense air movement by measuring impedance across the chest cavity.

The impedance measuring and processing circuits 278 communicate with the microcontroller 221, e.g., via control signals 280 and can be used for obtaining many types of bodily and intracardiac impedances, including a network of single- or multi-vector impedance measurements. Such impedance measurements can be used for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 278 may be coupled to the switch 226 so that any desired electrode may be used, and networks of vectors can be selected by the multi-vector network engine 238. The impedance measuring circuit 278 can also be used to obtain cardiogenic impedance signals that are compared to templates, in accordance with embodiments of the present invention. Additionally, the impedance measuring circuit 278 can be used to obtain cardiogenic impedance signals that are used to produce templates. Exemplary details of impedance measuring and processing circuits 278 are provided in FIG. 10, which is discussed below.

The exemplary implantable device 100 additionally includes a battery 276 that provides operating power to all of the components shown in FIG. 2. The battery 276 is preferably capable of operating at low current drains for long periods of time (e.g., less than 10 μA), and is capable of providing high-current pulses (for capacitor charging) when the patient requires a shock pulse (e.g., in excess of 10 A, at voltages above 500 V, for periods of 2-20 microseconds). The battery 276 also desirably has predictable discharge characteristics so that elective replacement time can be detected. As one example, the exemplary implantable device 100 employs lithium/silver vanadium oxide batteries.

The exemplary implantable device 100 can further include magnet detection circuitry (not shown), coupled to the microcontroller 221, to detect when a magnet is placed over the exemplary implantable device 100. A magnet may be used by a clinician to perform various test functions of the exemplary implantable device 100 and/or to signal the microcontroller 221 that an external programmer (e.g., 254) is in place to receive or transmit data to the microcontroller 221 through the telemetry circuits 264.

The microcontroller 221 further controls a shocking circuit 282 via a control signal 284. The shocking circuit 282 generates shocking pulses of low (e.g., up to 0.5 joules), moderate (e.g., 0.5-10 joules), or high energy (e.g., 11-40 joules), as selected by the microcontroller 221. Such shocking pulses are applied to the patient's heart 102 through at least two shocking electrodes selected, for example, from the left atrial coil electrode 322, the RV coil electrode 332, and/or the SVC coil electrode 334. As noted above, the case 200 may act as an active electrode in combination with the RV coil electrode 332, or as part of a split electrical vector using the SVC coil electrode 334 or the left atrial coil electrode 322 (i.e., using the RV coil electrode 332 as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 221 is capable of controlling the synchronous or asynchronous delivery of the shocking pulses.

The implantable device can also include a medication pump 286, which can deliver (e.g., titrate) medication to a patient, if triggered to do so. Information regarding exemplary implantable medication pumps may be found in U.S. Pat. No. 4,731,051 (Fischell) and in U.S. Pat. No. 4,947,845 (Davis), both of which are incorporated by reference herein. Delivering medication is an example of delivering treatment therapy.

More generally, the exemplary implantable device 100 can be programmed to stimulate different sets of vascular and cardiac muscles through the same lead/electrode system. The exemplary implantable device 100 can be programmed to vary the output voltage of various pulses to effectively stimulate different muscles of the heart and blood vessels, even though the physical placement of leads and electrodes does not change.

Impedance Signals

Figure 3:
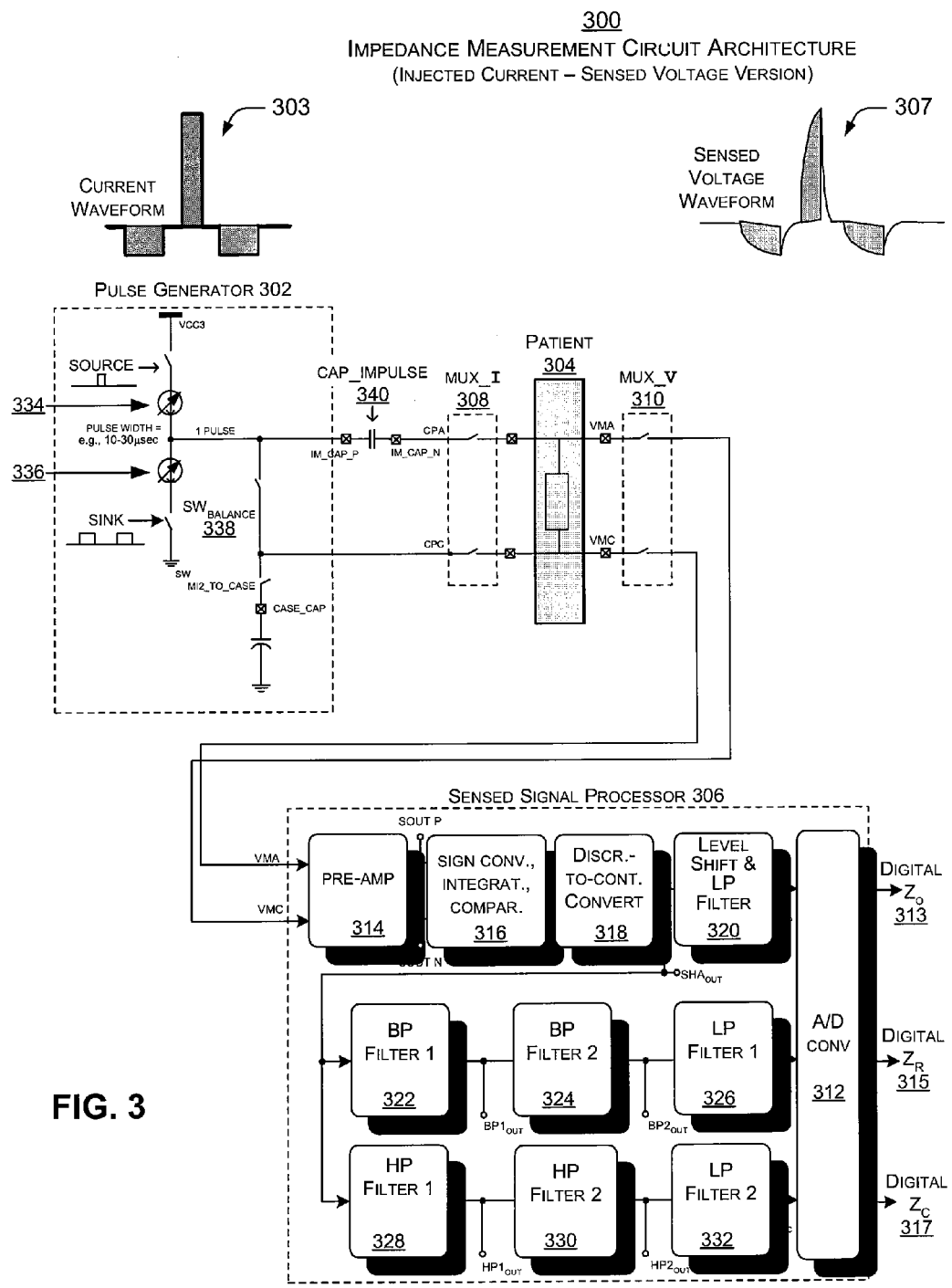
FIG. 3 is a block diagram of an exemplary impedance measuring circuit architecture.
Figure 4:
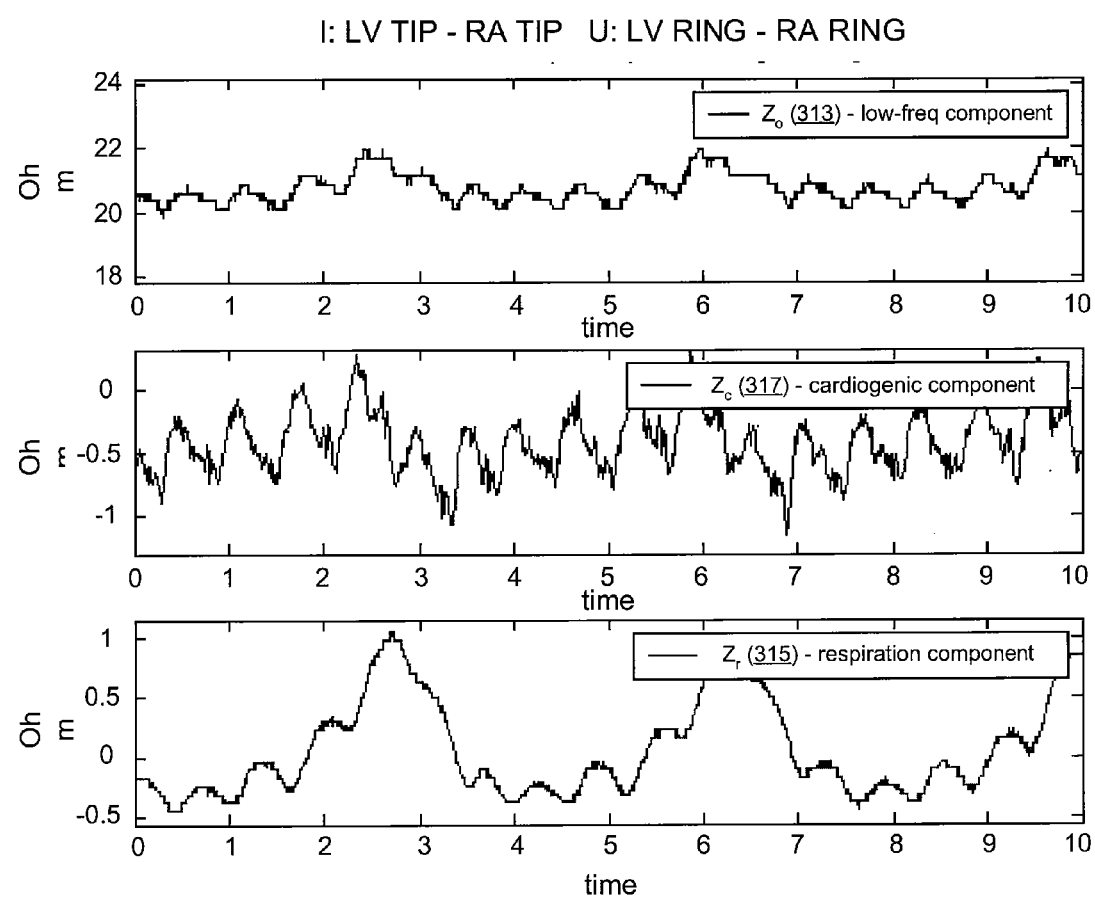
FIG. 4 illustrates exemplary low-frequency, cardiogenic and respirator impedance signals that can be produced using the circuit of FIG. 3.

Referring to FIG. 4, a raw impedance signal Z is shown filtered in three different ways to generate three different component signals. The raw impedance signal can be low pass filtered so that only the DC component is taken to yield a low-frequency impedance signal Zo 313, the raw impedance signal can be band-pass filtered with low cut-off frequencies to catch the respiratory component to yield a respiratory impedance signal Zr 315, and the raw impedance signal can be band-pass filtered with slightly higher cut-off frequencies to catch the cardiac component to yield a cardiogenic impedance signal Zc 317. Component signals Zo, Zc and Zr can be obtained at the output of the circuit in FIG. 3. It is noted that certain embodiments of the present invention as described herein rely specifically on variation in low-frequency impedance signals Zo to monitor zLAP; however, the present invention is not limited to use with low-frequency impedance signals, and alternatively may find application through use of cardiogenic impedance signals Zc, respiratory impedance signals Zr, and/or a combination of low-frequency, cardiogenic, and respiratory impedance signals, and the morphology of such signals. The invention is not limited to use with any specific component signal or form of the raw impedance signal. The following description is provided for completeness, so that the reader understands how such signals may be obtained.

Referring again to FIG. 2, the impedance processing module 240 and the impedance measuring and processing circuits 278 can be used to obtain impedance signals. Additionally, the vector engine 238 can assist in selecting electrodes for obtaining such signals. Exemplary details of a circuit architecture that can be used to obtain impedance signals are provided below with reference to FIG. 3. Additionally, the waveforms of FIG. 4 are used to explain the differences between low-frequency impedance signals, cardiogenic impedance signals and respiratory impedance signals.

In general, at least a pair of electrodes is used to deliver a stimulation waveform, and at least a pair of electrodes is used to measure the resulting voltage between electrodes, in order to obtain an impedance signal. Such a stimulation waveform preferably should not depolarize the myocardium, should cause only limited battery drain and should have a frequency with an acceptable signal to noise ratio. Exemplary stimulation waveforms, that are useful for obtaining impedance signals, are described in U.S. patent application Ser. No. 11/558,101, entitled "Systems and Methods to Monitor and Treat Heart Failure Conditions", (Yang et al), filed Nov. 9, 2006, which is incorporation herein by reference, and in U.S. patent application Ser. No. 11/684,664, entitled "Tissue Characterization Using Intracardiac Impedances with an Implantable Lead System", (Wong et al), filed Mar. 12, 2007, which is also incorporated herein by reference. As explained in the Yang et al. patent application, single- or multi-vector stimulation and sensing vectors can be used to obtain impedance signals. Additionally, as explained in the Yang et al. patent application, the electrode configurations for measuring impedance, e.g., across a pathway of bodily tissue, can be bipolar (a two node measurement), tripolar (a three node measurement), or quadpolar (a four node measurement), but are not limited thereto. The Yang et al. patent application also provides exemplary details of the impedance measuring and processing circuits 278, which can include, e.g., multiplexers and/or other switches, amplifiers, a signal conversion and integration module, a discrete-to-continuous signal conversion module, a level shift and low pass filter, various bandpass, low pass and high pass filters, and an analog-to-digital converter. However, less, alternative and/or additional components can be used.

As mentioned above, a single stimulation vector or multi-vector stimulation network and a single- or multi-vector sensing network can be used to deliver stimulation waveform(s) and obtain one or more impedance signals. Electrodes of conventional implantable lead systems and/or custom lead systems can be used to provide such stimulation and sensing networks. Exemplary electrodes of such leads were discussed above, with references to FIGS. 1 and 2.

For completeness, FIG. 3 shows an exemplary impedance measurement circuit architecture 300 (e.g., which can be used to implement block 278 on FIG. 2), including filters to obtain low-frequency, cardiogenic, and respiratory impedance signals. The illustrated architecture 300 is just one example configuration, other configurations are also possible. In one implementation, the exemplary impedance measurement architecture 300 includes a pulse generator 302 for generating an exemplary pulse waveform, in this case a current waveform 303, for application to the bodily tissue of a patient 304 and a sensed signal processor 306 for processing resulting waveforms detected in the tissue, in this case voltage waveforms 307. An injection (e.g., current pulse) multiplexor 308 implements the single- or multi-vector aspect of signal application by determining a first set of electrodes for injecting the exemplary waveform 303. The selection of electrodes may be determined by the vector engine 238 (FIG. 2). Likewise, a sensing (voltage measurement) multiplexer 310 implements signal sensing by determining a second set of electrodes for sensing the resulting voltage waveforms 307. The set of sensing electrodes may also be determined, e.g., by the vector engine 238 (FIG. 2). Both the injection multiplexor 308 and the sensing multiplexor 310 may be implemented in an implantable device 100 in the electrode configuration switch 226 (FIG. 2).

A waveform 303 for application to bodily tissue that is generated by the exemplary impedance measurement circuit architecture 300 possesses many special waveform features and electrical characteristics that are well suited for probing and measuring many types of physiological parameters in the body using current modulated or voltage modulated pulses. Such waveforms are described, as introduced above, in U.S. patent application Ser. No. 11/684,664, entitled "Tissue Characterization Using Intracardiac Impedances with an Implantable Lead System", (Wong et al), filed Mar. 12, 2007, and incorporated herein by reference. Exemplary waveforms 303 are multi-phasic, with negative phases (pulse segments below baseline) that balance positive phases (pulse segments above baseline). The illustrated waveform 303 is tri-phasic. Other versions of the waveform 303 may have more than three phases, may be synchronous or asynchronous, may be rectangular or sinusoidal, etc. One version of the waveform 303 uses the sin c(x) sampling waveform.

In one variation, the exemplary impedance measurement architecture applies the waveform 303 as a voltage waveform instead of a current waveform and senses the results as electrical current instead of voltage.

Properties of the exemplary waveforms 303 include superior penetration of some tissues than conventionally injected signals; better differential penetration of tissues than conventionally injected signals for improved differentiation and characterization of tissues; broader frequency spectrum content than conventionally injected signals in order to characterize tissue; greater neutrality in the body than conventionally injected signals, i.e., the exemplary waveforms do not change the parameter they are trying to measure, and moreover, do not create ionic imbalances or imbalances of charge, voltage, etc., in the tissues or at tissue-electrode interfaces.

Each waveform 303 preferably has a total duration less than the charging time constant of the electrode-electrolyte interfaces used to inject and sense the signals. These time constants are typically in the range of a few milliseconds. In one implementation, the duration of waveform 303 is less than 1 millisecond. This waveform feature is helpful for minimizing polarization effects at these electrode-electrolyte interfaces. Other features of the exemplary waveforms 303 include symmetric or asymmetric phase duration, decreasing phase amplitudes, and alternating phase signs. Each waveform 303 typically has null durations in between phases to provide time to allow complete processing of information caused by one phase before the next phase of the waveform 303 begins. Implementations of the waveform 303 that have near perfect square wave pulses (or rectangular wave pulses) contain a great deal of high-frequency content. Near-sinusoidal implementations of the waveform 303 may contain less high frequency content than the rectangular wave versions.

The features of exemplary waveforms 303 just enumerated provide numerous advantages, including: eliminating the need for fast digital sampling, minimizing artifacts introduced in the measurement process, increased tolerance of small phase delays between injected and sensed signals. The exemplary waveforms 303 also lend themselves to CMOS realization using low-value switched capacitor solutions. Further, the wide frequency spectrum of the injected signal can be used to implement algorithms that differentiate tissues based on their frequency response, and/or phase delay. The very low duty-cycle of the exemplary waveforms 303 make them safer for patients. The reduced duty-cycle brings the injected charge and the root-mean-square value of the injected signal well below levels that could be perceived by the patient or that could induce adverse events.

It is noted that the net-zero voltage feature, also referred to as the voltage-balanced feature, refers to the voltage formed on blocking capacitors that appear in series with the load. The flow of current through these capacitors builds up voltage across them. Since these capacitors, such as capacitor 340 in FIG. 3, also appear in circuits that are responsible for sensing cardiac activity, it is important that the net voltage built up on them be zero. As a result of the net-zero voltage feature, the influence of an exemplary waveform 303 on the circuits that sense cardiac activity is minimal.

Other features of the exemplary waveforms 303 derive from the above-mentioned null segments—intra-waveform segments containing no signal—that serve several purposes. First, the null segments allow the electronics in processing circuits to settle during measurement of phases and second, they allow multiple instances of the waveform 303 to exist in the patient's tissue simultaneously, being staggered by time multiplexing such that a phase of one waveform can be measured during the time that there is no signal between phases of another waveform.

In one implementation, the exemplary waveform 303 is used to derive physiological measurements based on impedances. Based on such impedance measurements, many physiological variables can be trended to detect changes in a patient's condition, such as congestive heart failure (CHF) index, pulmonary edema, systolic slope, contraction (e.g., dZ/dt(max)), diastolic slope, relaxation (e.g., dZ/dt(min)), pre-ejection period (in low resolution), ejection time, left ventricular ejection fraction (LVEF), diastolic heart failure index (DHFI), cardiac index, etc.

The exemplary waveform 303 provides an elegant and reliable vehicle for measuring bodily impedances in a manner that gives reliably reproducible results. Instead of a conventional technique of trying to sense an instantaneous measurement of a conventionally injected signal, the impedance measurement circuit architecture 300 derives an impedance measurement by dividing the area under the sensed voltage curve (waveform 307) by the area of the injected current waveform 303. An exemplary implantable device 100 can perform this exemplary method by "integrating the curve" of an absolute value of waveforms 303 or 307. Sometimes the exemplary implantable device can closely approximate this integration without having to perform an integration operation by directly measuring and summing the area "under" the curve (e.g., under the rectangular wave) of the waveform 303, that is, the area composed of the absolute value of the three areas of the three phases of an exemplary tri-phasic waveform 303.

Likewise, the exemplary implantable device can integrate, or closely approximate the integration, by measuring and summing the area "under" the curve (e.g., the rectangular wave) of the waveform 307, that is, the area composed of the absolute value of the three areas of the three phases. In one implementation, the area of the sensed voltage, waveform 307, is measured at the output of an integrator circuit. The area of the injected current, waveform 303, is computed by, or preset by, the microcontroller driving the implantable device. An implantable device 100 may thus use this area-based ("areal") approach to deriving a network of impedance measurements over a multi-vector network 310.

Returning to description of the impedance measurement circuit architecture 300 itself, the sensed signal processor 306 typically consists of pre-amplification circuitry, switched capacitor filters, and an analog to digital converter 312. In one implementation, the voltage signal from the voltage measurement multiplexer 310 is processed by several voltage measurement lines or paths. The illustrated sensed signal processor 306 is able to obtain at least the three different impedance signals introduced above with respect to FIG. 3, that is, low frequency impedance $Z_o$ 313, respiratory impedance $Z_r$ 315, and cardiogenic impedance $Z_c$ 317. Each measurement can be activated separately or simultaneously.

A digital form of low-frequency impedance $Z_o$ 313 may be obtained. First, the sensed signal, i.e., the tri-phasic voltage waveform 307 from the voltage measurement multiplexer 310, is sent to a preamplifier 314. The next stage is embodied in a sign conversion and integration module 316. At this stage, the signal is converted into an absolute value and then integrated over time. Using the integration process instead of conventional instantaneous measurements of impedance components such as pure resistance produces results that are more noise-free and more accurate than the conventional techniques.

The signal is then applied to a discrete-to-continuous signal conversion module 318. At this point in the architecture 300, the signals for low-frequency impedance $Z_o$ 313, respiration impedance $Z_r$ 315, and cardiogenic impedance $Z_c$ 317 are extracted separately by different filter paths, as summarized in FIG. 3. To obtain the low frequency impedance $Z_o$ 313, the signal is sent to a level shift and low pass filter module 320, and then to the analog to digital converter 312.

A digital form of the respiration impedance $Z_r$ 315 may be obtained by tapping the analog signal from the input of the level shift and low pass filter module 320, and feeding the signal to a line consisting of bandpass filters 322 and 324 and a low pass filter 326. The signal is then fed to the analog to digital converter 312 to obtain digital $Z_r$ 315.

A digital form of the cardiogenic impedance $Z_c$ 317 may likewise be obtained by tapping the analog signal from the input of the level shift and low pass filter module 320, and feeding the signal to a line consisting of high pass filters 328 and 330 and a low pass filter 332. The signal is then fed to the analog to digital converter 312 to obtain digital $Z_c$ 317.

In one implementation, the pulse generator 302 consists of two timing controlled current generators 334 and 336 with programmable magnitude. The first current generator 334 sources current, the other current generator 336 sinks the current. As part of the charge and voltage balancing process, the switch $SW_{Balance}$ 338 is used to discharge the external capacitor Cap_Impulse 340 after each generated impulse. The pulse rate is programmable.

Components of the impedance measurement architecture 300 may be distributed across the impedance measuring & processing circuits 278 (FIG. 2) and the impedance processing module 240 (FIG. 2). The distribution of components depends on implementation. That is, the exemplary impedance measurement architecture 300 may be implemented in hardware, software, or combinations thereof. For example, the exemplary impedance measurement architecture 300 may be implemented in hardware as part of the microcontroller 221 and/or as hardware integrated into the fabric of the exemplary implantable device 100; or as software/firmware instructions programmed into an implementation of the implantable device 100 and executed on the microcontroller 221 during certain modes of operation.

In one implementation, the preamplifier 314 is included in the impedance measuring & processing circuits 378. The pulse generator 302 can be implemented in the impedance processing module 340, as may some of the other components of the sensed signal processor 306.

Although the illustrated version of the impedance measurement circuit architecture 300 applies a current pulse waveform 303 and senses a voltage pulse waveform 307, other implementations can inject a voltage waveform and sense a current waveform.

The low-frequency component Zo 313 of a raw impedance measurement can be useful for determining extra- or intra-cardiac impedances and examining conditions such as pulmonary edema, and can be used in the various embodiments of the invention described in detail below with reference to FIGS. 5-10. The respiratory component Zr 315 of the raw impedance measurement can be useful for tracking respiration rate and depth, sleep apnea, and other related CHF conditions. The cardiogenic component Zc 317 of the raw impedance measurement can be separated out for tracking various hemodynamic parameters. Additionally, as above, it is possible that the respiratory component Zr 315, the cardiogenic component Zc 317, or any combination of the low-frequency component Zo 313, the respiratory component Zr 315, and the cardiogenic component Zc 317 can be used in the various embodiments of the invention described in detail below with reference to FIGS. 5-10.

FIG. 4 illustrates exemplary low-frequency, cardiogenic and respiration impedance signals that can be produced using the circuit of FIG. 3. As explained above, the cardiogenic and respiration impedance components represent variations about the reference line provided by the low-frequency impedance signal. These variations are shown as signed impedance (e.g. positive or negative deflections from low-frequency impedance values) and relate to effects of cardiac contractility and respiratory cycle, respectively.

It is noted that the term "based on", as used herein, means based at least in part on, unless stated otherwise. It is also noted that when certain portions of a signal, or the like, "are used" in a determination or analysis, other metrics and/or factors can also be used.

Affect of Posture on Impedance Signal

ZLAP can be calculated from impedance measured between two or more implanted electrodes, for example two or more implantable cardioverter-defibrillator (ICD) or cardiac resynchronization therapy defibrillator (CRT-D) lead electrodes. LAP estimation based on impedance is described in U.S. Pat. No. 5,003,976, entitled, "Cardiac and Pulmonary Physiological Analysis Via Intracardiac Measurements with a Single Sensor" (Alt), which patent document is incorporated herein by reference. Measurement of impedance can potentially offer less invasive estimates of LAP using an existing implanted device, such as an ICD or CRT-D. It therefore can be useful to improve the accuracy of zLAP as an estimate for directly measured LAP so as to reduce the need for supplemental device implantation which requires additional invasive procedures.

Figure 5A:
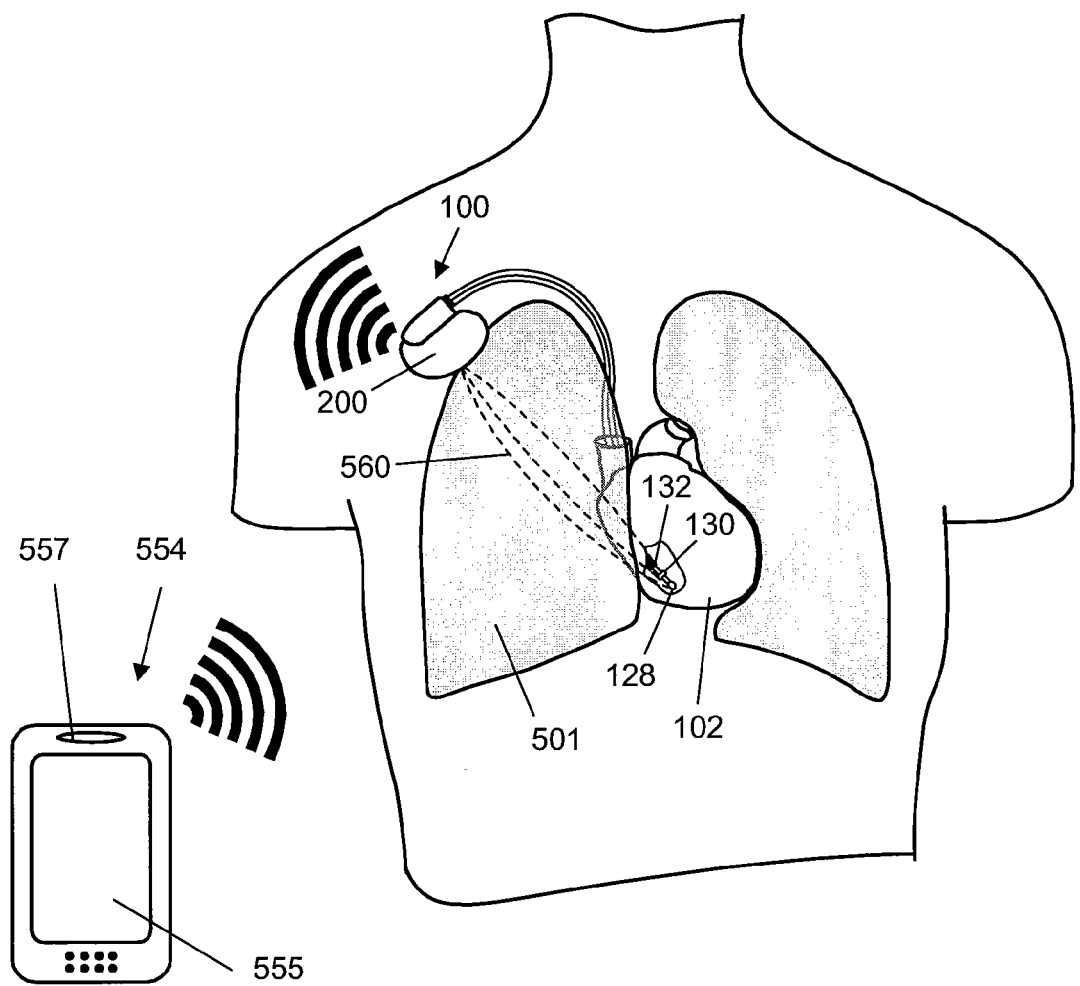
FIG. 5A is a diagram of the exemplary implantable device of FIG. 1 positioned near the right lung of a patient for measurement of zLAP, the exemplary implantable device communicating with a non-implanted device.
Figure 5B:
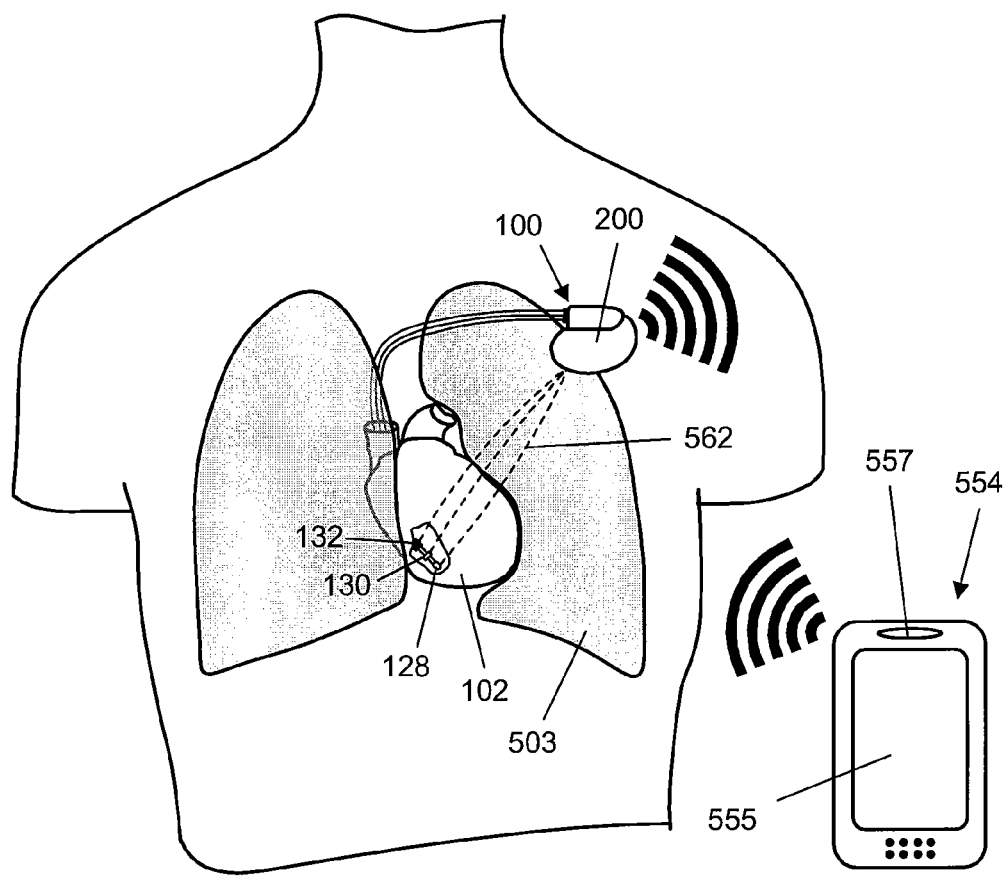
FIG. 5B is a diagram of the exemplary implantable device of FIG. 1 positioned near the left lung of a patient for measurement of zLAP, the exemplary implantable device communicating with a non-implanted device.

As mentioned above, indirect measurement of LAP relies on the fact that LAP is the primary force driving fluid from the intravascular space through the walls of the pulmonary capillaries into the extravascular space, and ultimately reaching the pulmonary alveolar space. In some embodiments of systems and methods in accordance with the present invention, zLAP calculation may benefit from measuring impedance across a patient's lung. Referring to FIG. 5A, an implantable device 100 is shown implanted in the right side of the patient's chest cavity so that vectors 560 generated between one or more lead electrodes positioned in the heart 102 (e.g., the electrodes 128, 130, 132 of the right ventricular lead, as shown) and the case 200 of the implantable device 100 intersect the right lung 501. An alternative arrangement is shown in FIG. 5B, wherein the implantable device 100 is shown implanted in the left side of the patient's chest cavity so that vectors 562 generated between one or more lead electrodes positioned in the heart 102 (e.g., the electrodes 128, 130, 132 of a right ventricular lead, as shown) and the case 200 of the implantable device 100 intersect the left lung 503. While the vectors 560, 562 of FIGS. 5A and 5B are shown substantially intersecting a single lung in isolation, the chosen vectors along which impedance is measured intersect additional tissue and structures of the body, and can intersect at least portions of both lungs, depending on the anatomy of the patient and the electrode(s) chosen to measure impedance.

As noted in U.S. patent application Ser. No. 11/863,516, entitled "Cardiogenic Impedance Waveform Morphology for Disease Monitoring," (Nabutovsky et al.), filed Sep. 28, 2007, which is also incorporated herein by reference, cardiogenic impedance Zc signals indicative of contractile activity of the heart, and respiratory impedance Zr indicative of respiratory cycles may be susceptible to activity (e.g., motion) and/or posture changes. Activity/position sensors 272 as described above and shown in FIG. 2 can be used to associate measured signals with detected posture, so that when comparisons are performed, a patient's posture is taken into account.

The present inventors have further observed that accuracy of zLAP calculations using low-frequency impedance Zo signals can be adversely affected by changes in a patient's posture prior to impedance measurement. In some embodiments of the present invention, zLAP can be calculated from low-frequency impedance Zo measurement(s) based on the following equation:

$$zLAP = \frac{A \times 1000}{Z_o} + B$$

where A is a first parameter and B is a second parameter.

Figure 6A:
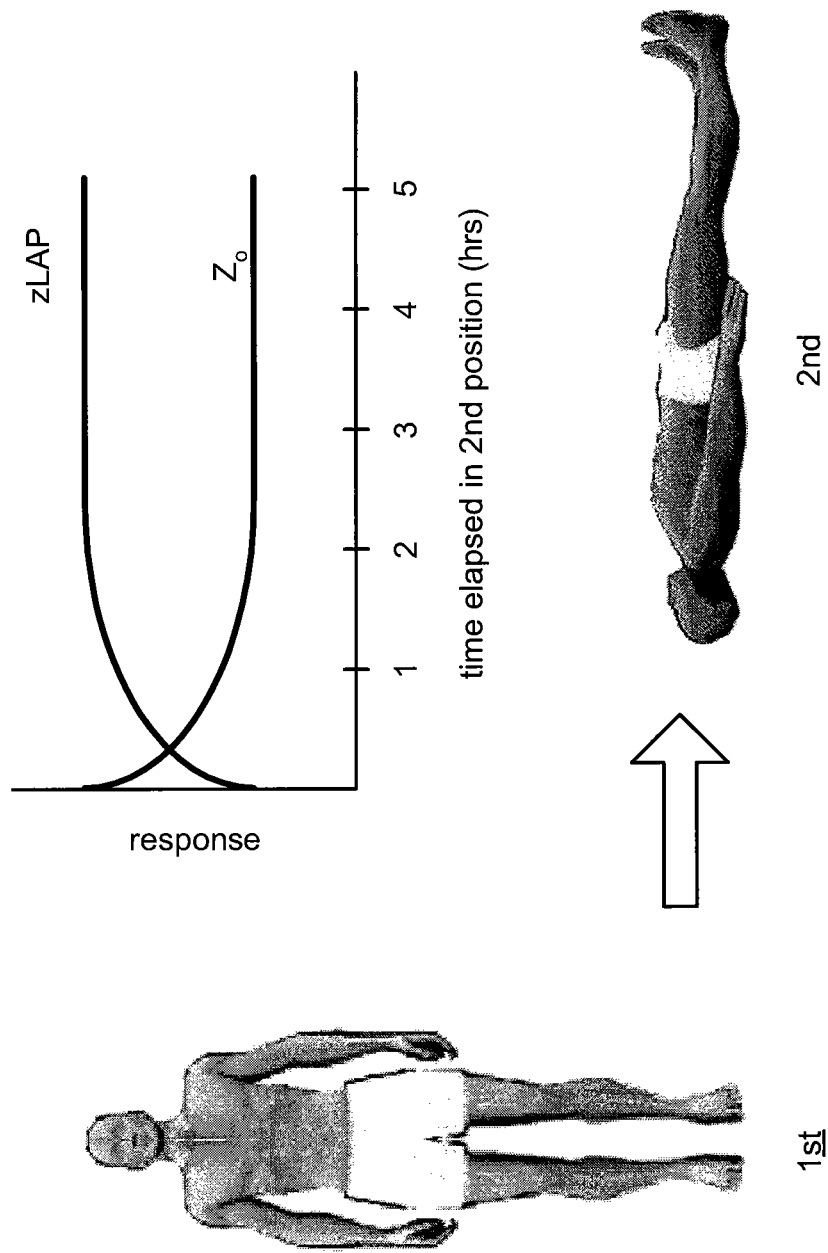
FIG. 6A is a qualitative graph illustrating exemplary settling in impedance signal and calculated zLAP after a change from a first, upright posture to a second, supine posture.
Figure 6B:
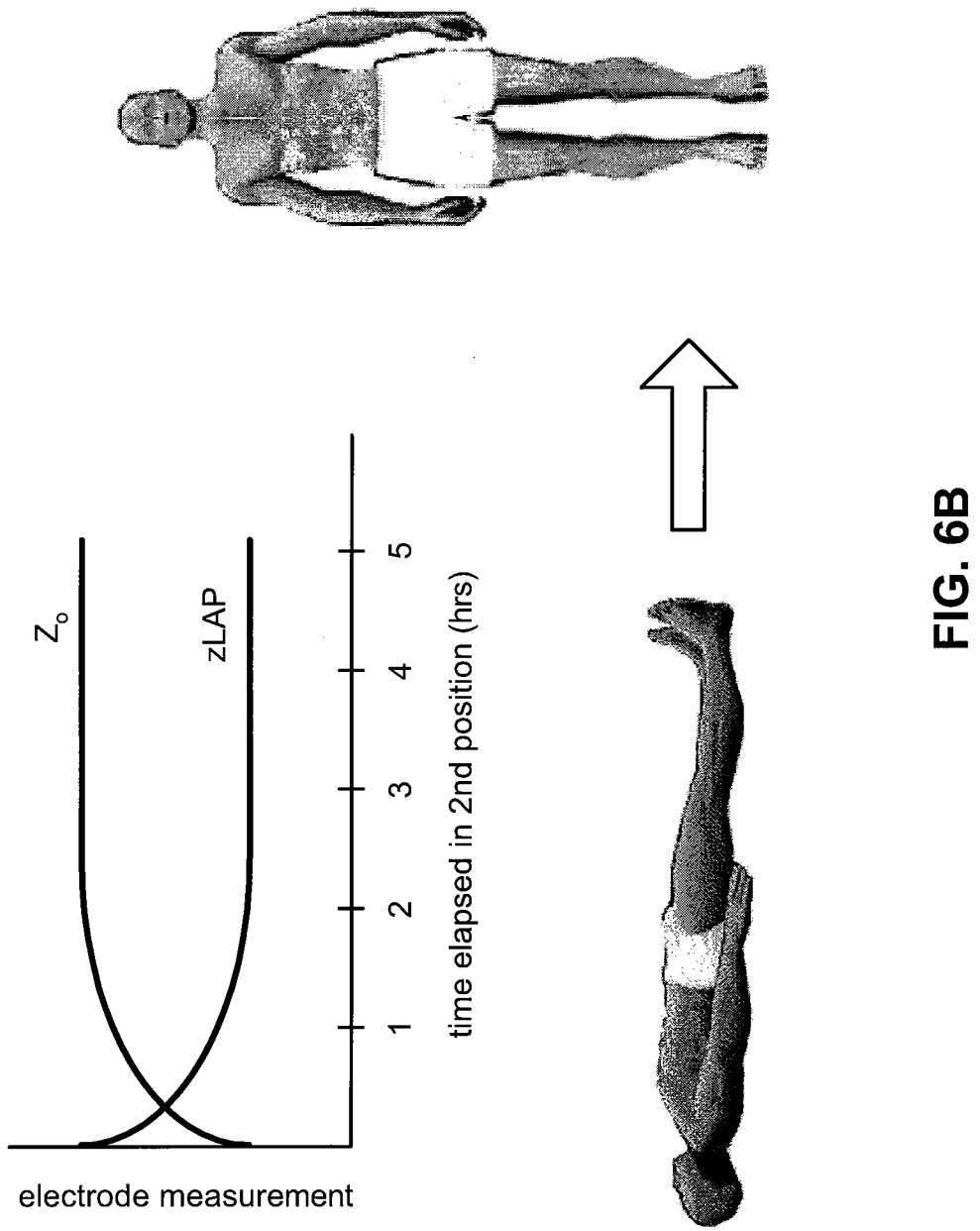
FIG. 6B is a qualitative graph illustrating exemplary settling in impedance signal and calculated zLAP after a change from a first, supine posture to a second, upright posture.

Referring to FIGS. 6A and 6B, examples of zLAP response to changes in posture from a first posture ($1^{st}$) to a second posture ($2^{nd}$) are shown. Responses for low-frequency impedance Zo and zLAP are exemplary and show trends over time. As such, y-axis values are not quantitative. A lag in time before a low-frequency impedance Zo signal generated along vectors between two or more electrodes reaches a general steady state has been observed. It is believed that such lag results from fluid accumulation in the lungs that occurs, for example, when a patient changes from an upright posture to a supine posture (as shown in FIG. 6A), or conversely from fluid drainage that occurs, for example, when a patient changes from a supine position to an upright position (as shown in FIG. 6B). Lag time can vary from patient to patient, depending on, but not limited to, patient anatomy and/or patient health. It has been observed that in general a lag of approximately two hours occurs from a time a change in posture occurs and an impedance signal obtainable across at least one lung generally achieves steady state. As will be appreciated from the mathematical relationship between zLAP and impedance, zLAP varies inversely with impedance.

Figure 6C:
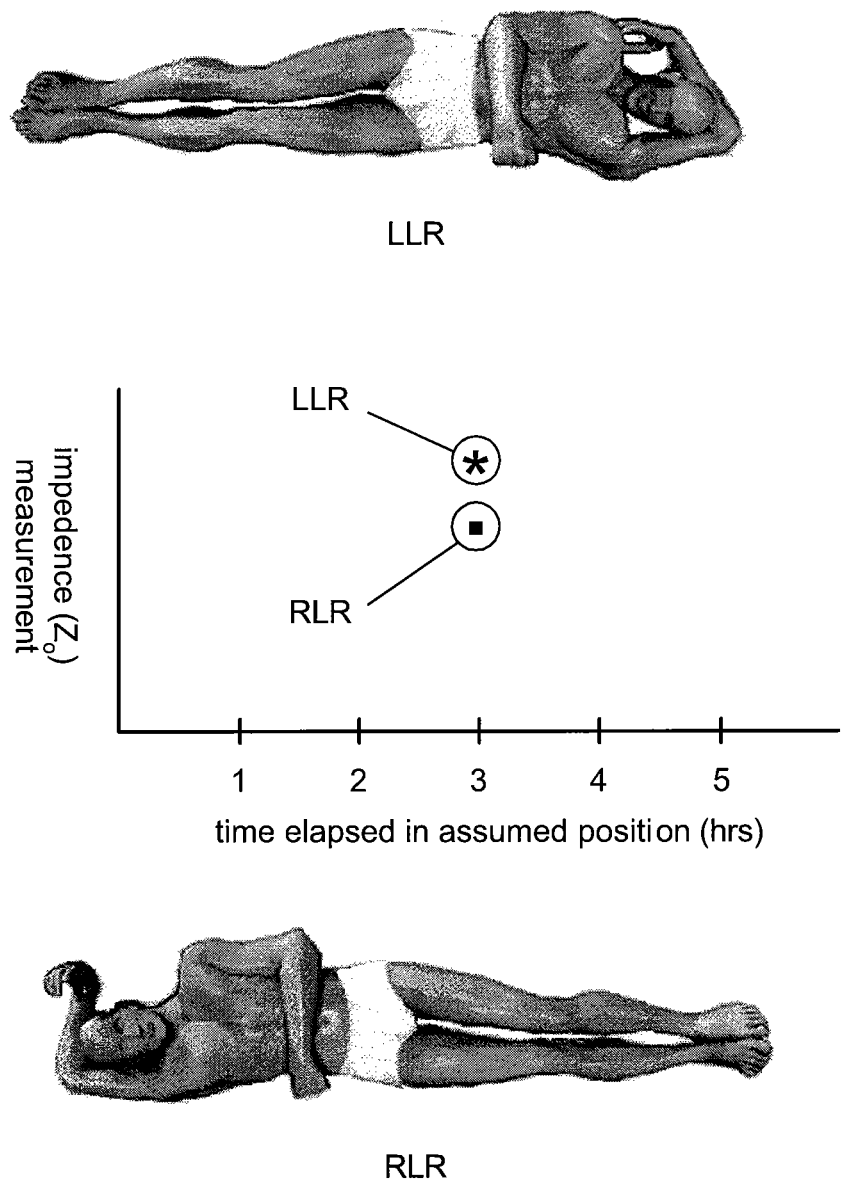
FIG. 6C is a qualitative graph illustrating an exemplary shift in impedance measurement associated with posture of a patient, with the patient assuming a left lateral recumbent posture for one impedance measurement and assuming a right lateral recumbent posture for a second impedance measurement.
Figure 6D:
FIG. 6D is a qualitative graph illustrating an exemplary shift in impedance measurement associated with posture of a patient, with the patient assuming a supine posture for one impedance measurement and assuming a prone posture for a second impedance measurement.
Figure 6D:
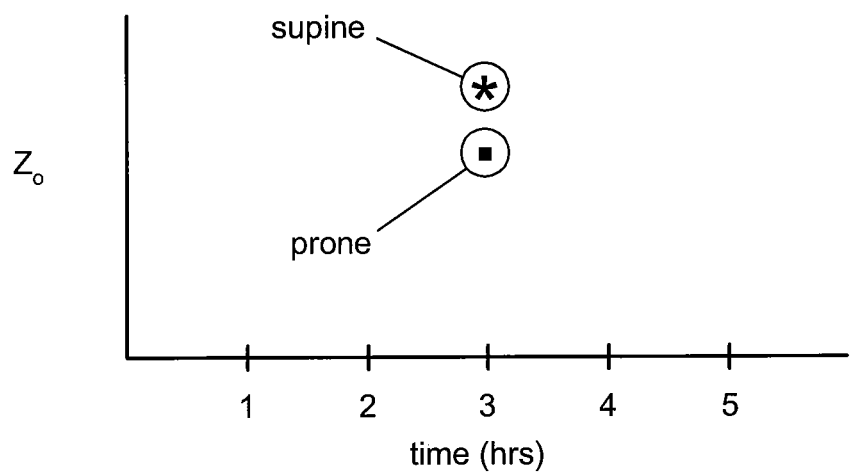
Figure 6D:

It has further been observed that movement from one prostrate position to another can affect an impedance signal measurement. Referring to FIG. 6C, a qualitative example of low-frequency impedance Zo signal measurement is shown with a patient in a right lateral recumbent position, or RLR, meaning that the patient is lying on his/her right side and a left lateral recumbent position, or LLR, meaning that the patient is lying on his/her left side. Again, the impedance measurement shifts with a change in position. Referring to FIG. 6D, a qualitative example of low-frequency impedance Zo signal measurement is shown with a patient in a supine position and a prone position with the measurement shifting with a change in position. It is believed that the shift in impedance measurement results at least in part from relative movement of the two or more electrodes used to measure impedance (e.g., relative movement between the case electrode and the RV tip electrode) and/or shifting of and stress on the patient's anatomical structures.

The present invention appreciates that accurate monitoring, diagnosis, and/or treatment can be adversely affected by inclusion of some data, for example data collected before an impedance signal generated along vectors between two or more electrodes has achieved a general steady state. Further, the present invention appreciates that monitoring changes in settling time and other impedance signal response to posture changes can assist in monitoring, diagnosis, and/or treatment of various pulmonary and/or cardiac conditions.

Preferred Embodiments

Figure 7:
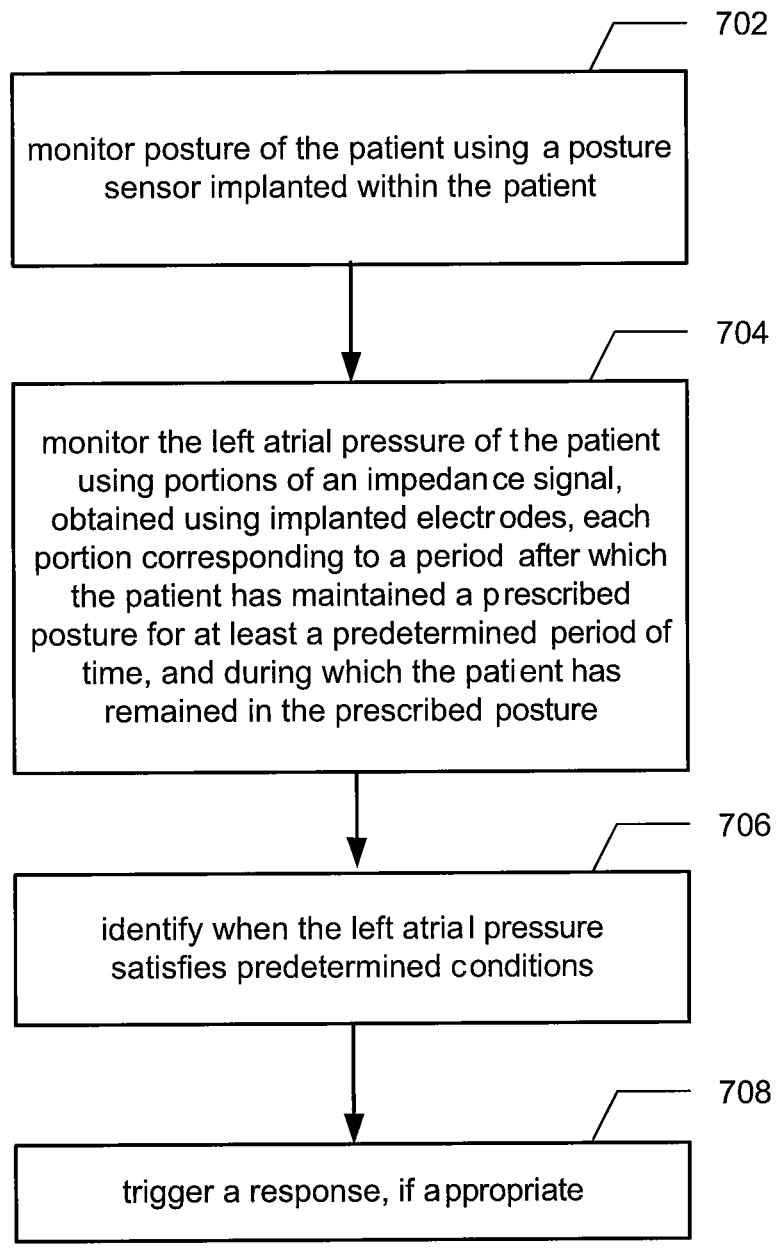
FIG. 7 is a high level flow diagram that is used to explain specific embodiments of the present invention, which are used to detect undesirably abnormal left atrial pressure and/or intra-thoracic fluid volume.
Figure 8:
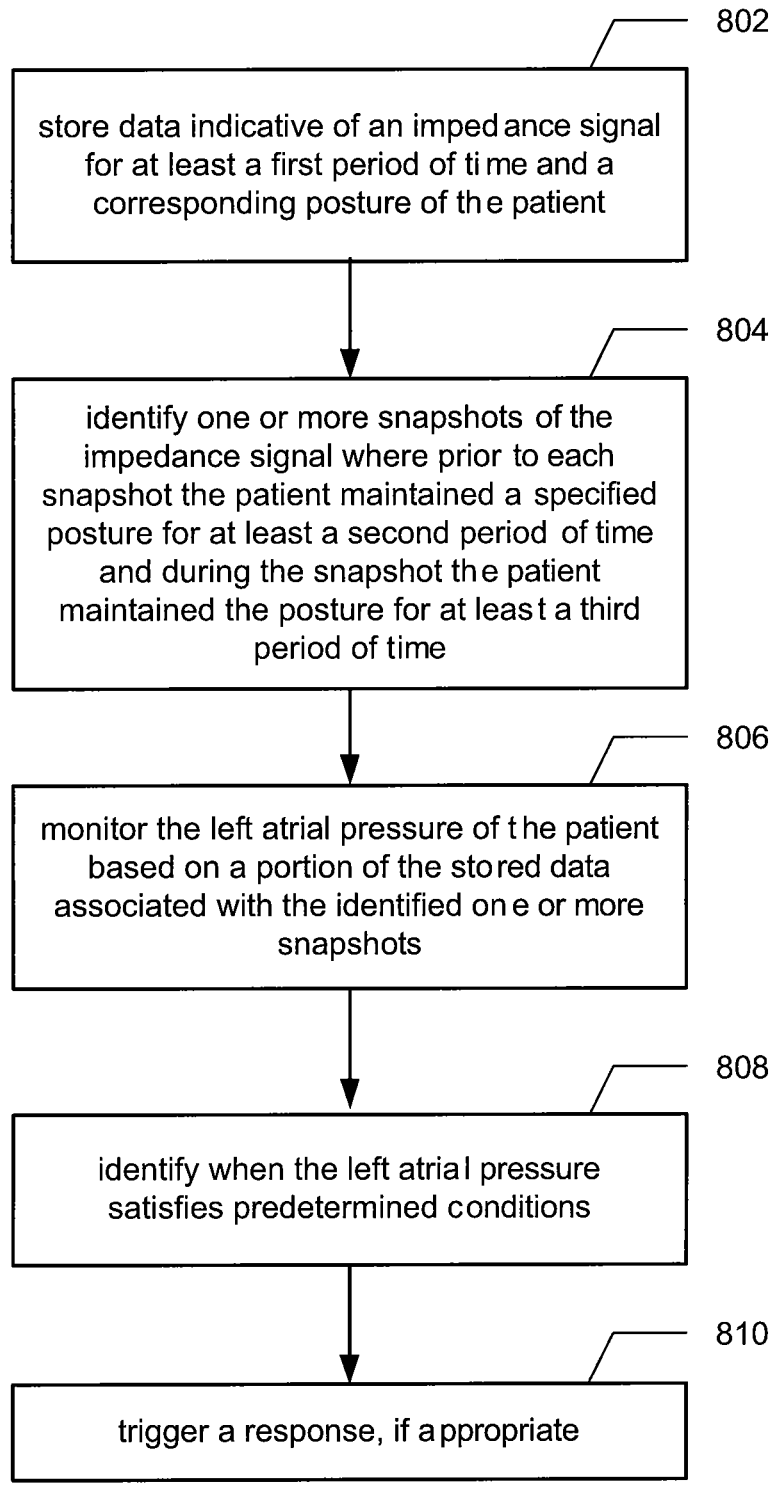
FIG. 8 is a high level flow diagram that is used to explain specific embodiments of the present invention, which are used to detect undesirably large degree of change in pulmonary edema.
Figure 10:
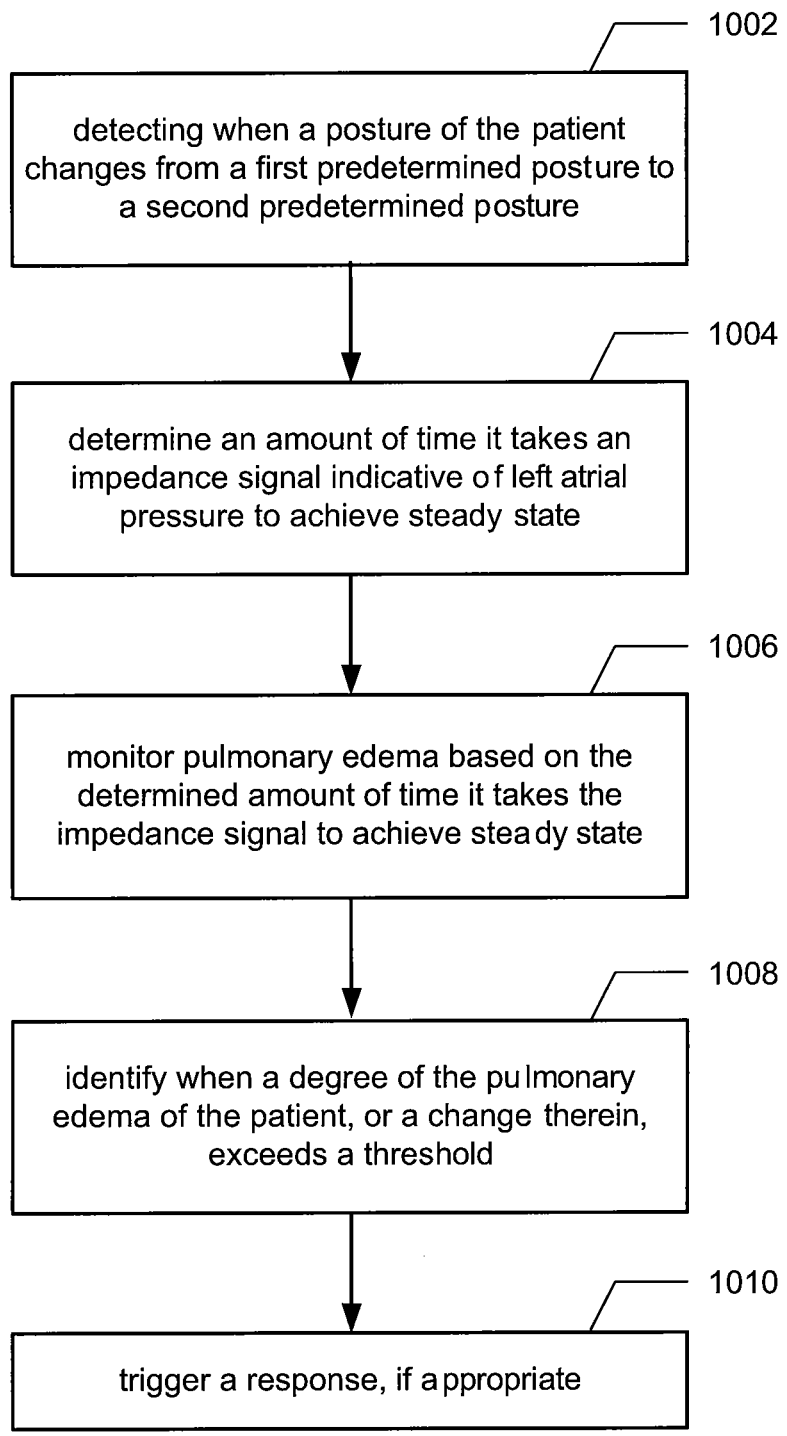
FIG. 10 is a high level flow diagram that is used to explain specific embodiments of the present invention, which are used to detect undesirably abnormal left atrial pressure and/or intra-thoracic fluid volume.

The high level flow diagrams of FIGS. 7, 8 and 10 will now be used to summarize various embodiments of the present invention. In the flow diagrams presented herein, the various algorithmic steps are summarized in individual "blocks." Such blocks describe specific actions or decisions that are made or carried out as the algorithm proceeds. Where a microcontroller (or equivalent) is employed, the flow diagrams presented herein provide the basis for a "control program" that may be used by such a microcontroller (or equivalent) to effectuate the desired control of an implantable device and/or an external device. Those skilled in the art may readily write such a control program based on the flow diagrams and other descriptions presented herein.

Referring to FIG. 7, an embodiment of a method in accordance with the present invention comprises monitoring LAP and/or intra-thoracic fluid volume of a patient to identify when the LAP and/or intra-thoracic fluid volume is undesirably abnormal. Alternatively, or additionally, LAP and/or intra-thoracic fluid volume of a patient can be monitored to identify when the LAP and/or intra-thoracic fluid volume is normal, for example to determine the efficacy of treatment or to adjust pacing parameters. The method includes qualifying measurements of impedance signals for use in calculating zLAP to estimate LAP. At step 702, the posture of the patient is monitored using a posture sensor, for example a 3D accelerometer. While the posture sensor has been described above as a component of an implantable device including two or more electrodes for measuring impedance, in other embodiments the posture sensor can be a separately implantable device or a component of a separately implantable device, a subcutaneously implantable device or a component of a subcutaneously implantable device, or a non-implanted device that is capable of monitoring posture. Although the posture sensor will be described hereafter as a 3D accelerometer associated with the implantable device, a non-implanted device could conceivably use techniques other than accelerometer-based techniques. For example, where impedance signal measurements are taken while the patient is in a supine position, the posture sensor could conceivably comprise sensors within the surface upon which the patient rests, or alternatively the posture sensor could be a camera connected with a computer and capable of visually distinguishing between postures.

At step 704, LAP is monitored based on zLAP calculated using qualified impedance signal measurements. zLAP can be calculated within a module of the controller (e.g., LAP monitor 239) or alternatively, qualified impedance signal measurements can be recorded and communicated to an external device such as an external programmer or a dedicated monitoring station for calculating zLAP. Qualified impedance signal measurements can be portions of an impedance signal obtained using two or more implanted electrodes that correspond to a period after which the patient has maintained a prescribed (or otherwise predetermined) posture for at least a predetermined period of time, and during which the patient has remained in the prescribed posture. The prescribed posture can be any posture prescribed by a physician. Prescribing a posture can provide consistency between multiple different impedance signal measurements separated over time, preventing deviations in estimates of left atrial pressure unrelated to and/or falsely indicative of conditions of interest, such as organ health. As illustrated in FIGS. 6A through 6D, posture can affect impedance signal measurement by causing changes in the relative positions of electrodes used for measurement, changes in fluid accumulation in tissues through which impedance is measured, and/or other physiological and anatomical factors.

The prescribed posture may depend on various factors, and need not be confined to a choice between prone and upright posture. For example, a patient may favor sleeping on his/her right side; therefore, it may be desirable to prescribe a right lateral recumbent posture for obtaining impedance signal measurements while the patient is sleeping. The predetermined period of time for which the patient generally maintains the prescribed posture or approximately the prescribed posture can be based on the posture prescribed and a period of lag between the assumption of the prescribed posture and achievement of a substantially steady state impedance. The predetermined period of time can vary depending on a posture held by the patient prior to the prescribed posture. For example, the predetermined period of time for the patient illustrated in FIG. 6A who moves from an upright posture to the prescribed supine posture is about two hours; however, in FIG. 6C, the time it takes to reach steady state impedance following a change from left side recumbent position to right side recumbent position may be considerably shorter. The predetermined period of time can also vary between patients.

In still further embodiments, a specific posture need not be prescribed prior to measurement. Rather, the posture sensor can be used to determine that any posture has been maintained for a period of time associated with that particular posture and obtain impedance signal measurements designated as being obtained for that particular posture. The process of obtaining impedance signal measurements can continue for any designated period of time, resulting in information being collected for some or all postures that have been maintained according to appropriate criteria. The physician or patient can then prescribe a posture for which data is recalled from storage. The data can be collectively downloaded to an external device providing additional data points for later review. Further, data collected for different postures can be compared to identify trends or maintain a profile of the patient's physiology.

If the prescribed posture is an upright posture, it may be desirable to further screen or characterize impedance signal measurement by analyzing patient motion. For example, using data from a 3D accelerometer, distance traveled in three axes can be calculated by double integration of the accelerometer signal. If any of the distance exceeds a travel rate criterion (e.g., X inches per Y seconds), then the implantable device can choose not to collect an impedance signal measurement or may flag the impedance signal measurement, or still further may postpone impedance signal measurement for a designated amount of time, or a time calculated based on the travel rate calculation.

In some embodiments, a posture change event from the prescribed posture to a non-prescribed posture may not necessarily render an impedance signal measurement disqualified if the period of changed posture is brief such that fluid accumulation/drainage is sufficiently small, and other anatomical and/or physiological effects are sufficiently small so as to be recovered by the resumption of the prescribed position without unacceptably extending the achievement of substantial steady state impedance signal response beyond the predetermined period of time. Algorithms can be applied by a module of the controller, for example, or some other circuitry of the implantable device to determine the affect of posture change events that occur within the prescribed period of time on the achievement of steady state response in the impedance signal. In still other embodiments, algorithms can be applied to calculate a delay in impedance signal measurement as a result of the posture change event.

The length of time of each portion of the impedance signal monitored, during which the patient remains in the prescribed posture or in approximately the prescribed posture, can also vary depending on the prescribed posture. Generally, a length of time of two seconds can be sufficient to capture a usable impedance signal measurement, although the length of time can be shorter or longer.

Impedance signal measurements can be obtained simultaneously or staggered in time along multiple different vectors between two or more electrodes. For example, in FIG. 5A, multiple vectors 560 are illustrated between the case electrode 200 and electrodes 128, 130, 132 of a right ventricular lead. Multiple impedance signal measurements obtained along multiple vectors can be averaged to obtain impedance for use in zLAP calculation. In some embodiments, the average can be calculated by weighing measurements along some vectors more than others. Further, multiple impedance signal measurements can be used to remove measurements obtained along one or more vectors that are inconsistent with the measurements obtained along the other vectors, for example due to noise. In an embodiment, impedance signal measurements from six vectors are obtained for use in calculating zLAP. In other embodiments, impedance signal measurements can be obtained along as few as a single vector, to as many vectors as can be managed by the impedance processing module 240 and/or impedance measuring and processing circuits 278 while providing useful zLAP calculation.

At step 706, the left atrial pressure and/or intra-thoracic fluid volume is identified as satisfying one or more predetermined conditions when zLAP calculations meet criteria for indicating a likely monitored-for result. For example, in an embodiment, the left atrial pressure and/or intra-thoracic fluid volume is identified as undesirably abnormal when zLAP calculations meet criteria for indicating a likely undesirable result. The criteria can be, for example, a deviation from a previous measurement by a predefined amount and/or trending of measurements symptomatic of organ damage and/or failure. In an alternative embodiment, the monitored-for result can be a response to treatment. The left atrial pressure and/or intra-thoracic fluid volume is identified as normal or abnormal as zLAP calculation meet respective criteria for indicating response to treatment. In this way, efficacy of treatment such as prescription of medicine, for example, can be monitored. The monitored-for result and the criteria met can determine a response. In a still further embodiment, the left atrial pressure and/or intra-thoracic fluid volume can be monitored to assess responsiveness to pacing.

At step 708, a response can be triggered if appropriate, that is, if the monitored-for result and criteria indicate that a response be triggered. For example, if monitoring of LAP and/or intra-thoracic fluid volume for abnormality is performed by circuitry of the implantable device and such abnormality is identified, the implantable device can trigger a response by applying corrective treatment and/or providing a warning signal to the patient or the patient's physician by sending the warning signal and/or appropriate data to an external device. If monitoring the LAP and/or intra-thoracic fluid volume is performed to assess efficacy of treatment, the implantable device can respond by sending data assessment data to an external device. If monitoring LAP and/or intrathoracic fluid volume is performed to assess responsiveness to pacing, the implantable device can respond to deviations in measurements by adjusting cardiac pacing parameters. Alternatively, LAP monitoring can be used to adjust therapy, for example medication based on a formula predefined by a physician can be adjusted. Patient can view this update on a hand held device 550 such as shown in FIGS. 5A and 5B. Alternatively, electrical therapy administered by an implantable cardioverter-defibrillator (ICD) or cardiac resynchronization therapy defibrillator (CRT-D) can be automatically adjusted.

A telemetry circuit (264, FIG. 2) of the implantable device 100 can communicate a warning signal via a communication link 266 to the external device 254. As shown in FIGS. 5A and 5B, the external device 254 can be a handheld device. The external device 254 can be a dedicated tool or alternatively the external device 254 can be a commercially available personal digital assistant (PDA), mobile phone, or other electronic device capable of communicating to the implantable device 100 by way of a communication link 266, and capable of communicating a warning to the patient and/or the patient's physician. For example, several mobile phone manufacturers, such as Apple, Inc., have begun to partner with or open their platforms to manufacturers of medical diagnostic tools to create software applications that enable mobile phones to communicate with medical diagnostic tools through wireless protocols or through peripheral attachments to the mobile phone in order to collect and/or analyze data obtained by the medical diagnostic tools for display by the mobile phone and/or delivery by the mobile phone to the patient's physician using a cellular network and/or the internet, for example.

The external device 554 can communicate a warning signal to the patient using a visual warning on a display screen 555 or an audible warning emitted from a speaker 557. Embodiments of the present invention are not intended to be limited to the embodiments set forth in FIGS. 5A and 5B. One of ordinary skill in the art will appreciate, upon reflecting on the teaching contained herein, the myriad different ways in which a patient and/or physician can be alerted to an abnormality by an implantable device capable of establishing a communication link via a telemetry circuit.

FIG. 8 illustrates an alternative embodiment of a method in accordance with the present invention comprising monitoring left atrial pressure and/or intra-thoracic fluid volume of a patient, e.g., to identify when the left atrial pressure and/or intra-thoracic fluid volume is undesirably abnormal. The method includes qualifying measurements of impedance signals for use in calculating zLAP to estimate left atrial pressure. At step 802, data indicative of an impedance signal between two or more electrodes for a period of time is stored. The posture of the patient contemporaneous with the impedance signal data is detected using a posture sensor, for example a 3D accelerometer, and stored as posture data. As in the method of FIG. 7, the posture sensor need not be a component of the implantable device; however, the posture data should be temporally mapped, or capable of being temporally mapped, to the impedance signal data with a degree of accuracy that generally produces de minimis errors in zLAP calculation resulting from inaccurate qualification of impedance signal measurements.

Data indicative of an impedance signal can be stored in memory of the implantable device, such as the memory 260 for use in storing programmable operating parameters used by the microcontroller 221 of FIG. 2 or in additional dedicated memory (not shown) within the implantable device. Likewise, posture data can be stored in common memory with the data indicative of impedance signal, in dedicated memory, or alternatively in memory associated with a housing of a posture sensor separate from the implantable device (in embodiments where the posture sensor is separate from the implantable device). Still further, data indicative of an impedance signal and/or posture data can be communicated to an external device in real time, or in time-shifted fashion to an external device 254 for storage via a communication link 266. While embodiments of the present invention can benefit from use of existing implantable devices, and therefore can benefit from use of existing elements such as memory 260, the technique by which data is stored should not be limited by the description provided herein. One of ordinary skill in the art, upon reflecting on the teachings provided herein, will appreciate the myriad ways in which data can be retained at least temporarily for analysis.

At step 804, one or more snapshots of the impedance signal are identified from the stored data indicative of an impedance signal where prior to each snapshot the patient maintained a specified posture for at least a specified period of time (e.g., 2 hours) and during the length of time of the snapshot the patient maintained the specified posture or approximately the specified posture. Generally, a snapshot having a length of time of two seconds is sufficient for use in calculating zLAP, although the length of time can be shorter or longer. Once the one or more snapshots of the impedance signal are identified, the method can optionally include erasing stored data or permitting overwrite of stored data other than the data associated with the identified one or more snapshots. Erasing or permitting overwrite of data can reduce the consumption of memory capacity of the implantable device in performing the method. Alternatively, the stored data can be scheduled to be off-loaded to an external device, for example, whenever the external device and the implantable device are synced, thereby maintaining the stored data for further analysis or for verification. Off-loaded data can then be erased or overwritten. Alternatively, stored data associated with identified snapshots can be off-loaded to an external device, and all data stored in memory can be erased or overwritten.

At step 806, left atrial pressure is monitored based on zLAP calculated using the portion of the stored data indicative of impedance signal measurements associated with the identified one or more snapshots. zLAP can be calculated within a module of the controller or alternatively, zLAP can be calculated by an external device such as an external programmer or a dedicated monitoring station for calculating zLAP. The specified posture can be any posture that provides consistency between multiple different impedance signal measurements separated over time, preventing deviations in estimates of left atrial pressure unrelated to and/or falsely indicative of conditions of interest, such as organ health.

As above, posture can be specified for multiple different reasons, and need not be confined to a choice between prone and upright posture. For example, the posture can be specified based on a patient's sleeping habits/patterns. The predetermined period of time for which the patient generally maintains the specified posture or approximately the specified posture can be based on the posture specified and a period of lag between the assumption of the specified posture and a substantially steady state impedance signal response. The predetermined period of time can vary depending on a posture held by the patient prior to the specified posture. For example, the predetermined period of time for the patient illustrated in FIG. 6A who moves from an upright posture to the specified supine posture is about two hours; however, in FIG. 6C, the time it takes to reach steady state impedance following a change from left side recumbent position to right side recumbent position may be considerably shorter. The predetermined period of time can also vary between patients.

Also as above, no specific posture needs to be prescribed for obtaining snapshots. Rather, the posture sensor, a module of the implantable device receiving posture information from the posture sensor, or an external device, can be used to determine that any posture has been maintained for a period of time associated with that particular posture, and this determination can be used to identify a snapshot for that particular posture.

Further, if the prescribed posture is an upright posture, it may be desirable to further characterize a snapshot (or disqualify a snapshot) by analyzing patient motion. For example, using data from a 3D accelerometer, distance traveled in three axes can be calculated by double integration of the accelerometer signal. If any of the distance exceeds a travel rate criterion (e.g., X inches per Y seconds), then the implantable device can choose not to identify the data as a snapshot or may flag a snapshot, or further designate the snapshot to data collected after a designated amount of time has passed, or an amount of time calculated based on the travel rate calculation.

In some embodiments, a posture change event from the specified posture to a non-specified posture may not necessarily render an impedance signal measurement disqualified if the period of changed posture is brief such that fluid accumulation/drainage is sufficiently small, and other anatomical and/or physiological effects are sufficiently small so as to be recovered by the resumption of the specified posture without unacceptably extending the achievement of substantially steady state impedance signal response beyond the predetermined period of time. Algorithms can be applied by a module of the controller, for example, or some other circuitry of the implantable device to determine the affect of posture change events that occur within the specified period of time on the achievement of steady state response in the impedance signal. In still other embodiments, algorithms can be applied to calculate a delay in impedance signal measurement as a result of the posture change event.

As described above, impedance signal measurements can be obtained simultaneously or staggered in time along multiple different vectors between two or more electrodes. For example, multiple vectors 560 are shown between the case electrode 200 and electrodes 128, 130, 132 of the right ventricular lead of FIG. 5A.

At step 808, the left atrial pressure and/or intra-thoracic fluid volume is identified as satisfying one or more predetermined conditions when zLAP calculations meet criteria for indicating a likely monitored-for result. For example, in an embodiment, the left atrial pressure and/or intra-thoracic fluid volume is identified as undesirably abnormal when zLAP calculations meet criteria for indicating a likely undesirable result. The criteria can be, for example, a deviation from a previous measurement by a predefined amount and/or trending of measurements symptomatic of organ damage and/or failure. In an alternative embodiment, the monitored-for result can be a response to treatment. The left atrial pressure and/or intra-thoracic fluid volume is identified as normal or abnormal as zLAP calculation meet respective criteria for indicating response to treatment. In this way, efficacy of treatment such as prescription of medicine, for example, can be monitored. The monitored-for result and the criteria met can determine a response. In a still further embodiment, the left atrial pressure and/or intra-thoracic fluid volume can be monitored to assess responsiveness to pacing.

At step 810, a response can be triggered if appropriate, that is, if the monitored-for result and criteria indicate that a response be triggered. For example, if monitoring of left atrial pressure and/or intra-thoracic fluid volume for abnormality is performed by circuitry of the implantable device and such abnormality is identified, the implantable device can trigger a response by applying corrective treatment and/or providing a warning signal to the patient or the patient's physician by sending the warning signal and/or appropriate data to an external device. If monitoring the left atrial pressure and/or intra-thoracic fluid volume is performed to assess efficacy of treatment, the implantable device can respond by sending data assessment data to an external device. If monitoring the left atrial pressure and/or intra-thoracic fluid volume is performed to assess responsiveness to pacing, the implantable device can respond to deviations in measurements by adjusting cardiac pacing parameters. Alternatively, LAP monitoring can be used to adjust therapy, for example medication based on a formula predefined by a physician can be adjusted or electrical therapy administered by an implantable cardioverter-defibrillator (ICD) or cardiac resynchronization therapy defibrillator (CRT-D) can be adjusted.

As above, a telemetry circuit 264 of the implantable device 100 can communicate a warning signal and/or appropriate data to an external device 254 via a communication link 266 and the external device 254 can communicate a warning signal to the patient using a visual warning on a display screen 552, an audible warning emitted from a speaker 556, and/or any other of myriad different ways that would be appreciated by one of ordinary skill in the art, upon reflecting on the teaching contained herein.

Figure 9:
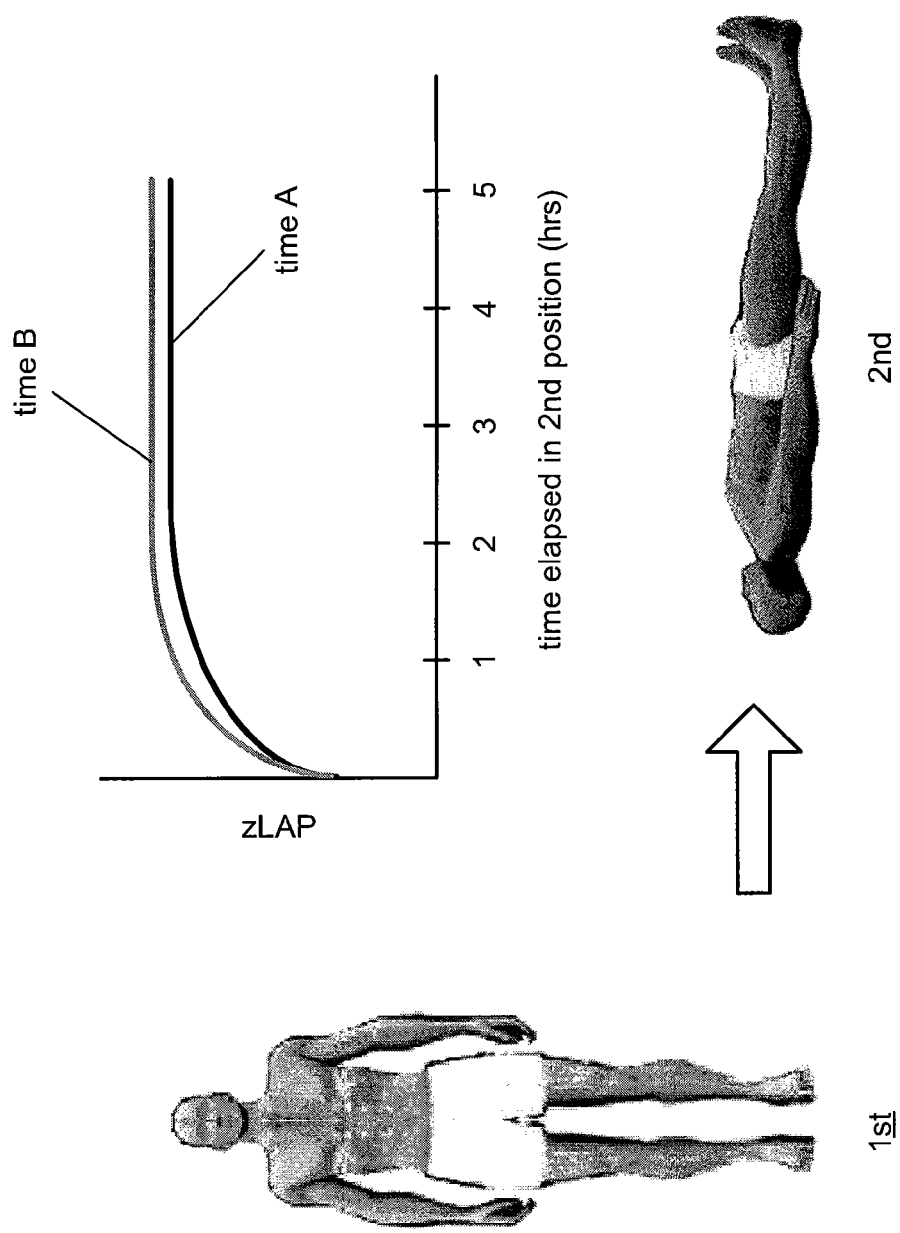
FIG. 9 is a qualitative graph illustrating an exemplary shift in exemplary settling in impedance signal after a change from a first, upright posture to a second, supine posture over a period in time indicative of pulmonary edema.

Referring to FIGS. 9 and 10, embodiments of methods in accordance with the present invention can further be applied to identify shifts in responses of impedance signals to changes in posture over time in order to monitor and/or diagnose disorders. Such shifts may or may not result in zLAP calculations that identify undesirably abnormal left atrial pressure and/or intra-thoracic fluid volume. A change of fluid accumulation rate may be used as an indicator of patient health. For example, in some embodiments a measured fluid accumulation rate can be compared with a reference fluid accumulation rate observed is under known condition (e.g, a stable condition with no HF exacerbation). If the measured fluid accumulation rate deviates from the reference fluid accumulation rate significantly, an alarm can be generated. In still further embodiments, a change in fluid accumulation rate over time can be monitored so that a reference value need not be used. For example, a shift in results indicating faster fluid accumulation rate when a patient moves from standing to supine can indicate that the patient's condition is worsening, while a shift in results indication faster fluid accumulation rate when a patient moves from supine to standing can indicate that the patient's condition is improving. Fluid accumulation rate can differ at various phases before a pulmonary edema event, meaning initially the fluid accumulation rate can be fast because the interstitial space is dry, but the fluid accumulation rate slows when the interstitial space is filled with fluid.

FIG. 9 is a qualitative graph illustrating an exemplary shift in exemplary settling in an impedance signal after a change from a first, upright posture to a second, supine posture over a period of time. The exemplary impedance signal captured first is designated "time A" and the exemplary impedance signal captured second is designated "time B." The time B trace has a steeper curve and reaches steady state sooner than the time A trace. The time B trace may be explained by more rapid accumulation of fluid in the lung through which the vector(s) used to generate the time B trace intersects. Rapid accumulation of fluid when moving from an upright posture to a supine posture can be indicative of pulmonary edema due to either failure of the heart to remove fluid from the lung circulation ("cardiogenic pulmonary edema") or a direct injury to the lung parenchyma ("non-cardiogenic pulmonary edema"). Pulmonary edema leads to impaired gas exchange and may cause respiratory failure. An upward shift in the time B trace is also observed, and can be attributable to increased fluid in the alveolar walls, increased vascular filling, pleural effusions, and upper lobe diversion (increased blood flow to the higher parts of the lung).

Referring to FIG. 10, an embodiment of a method in accordance with the present invention comprises monitoring for pulmonary edema in a patient to identify when a degree of pulmonary edema or a change therein exceeds a threshold. At step 1002, the posture of the patient is monitored using a posture sensor, for example a 3D accelerometer, to detect when the posture of the patient changes from a first predetermined posture to a second predetermined posture. As in the method of FIGS. 7 and 8, the posture sensor need not be a component of the implantable device. At step 1004, once the posture sensor detects that the posture of the patient changes from the first predetermined posture to the second predetermined posture, an amount of time that it takes an impedance signal indicative of left atrial pressure and/or intra-thoracic fluid volume to achieve steady state is determined.

As noted above, a change from an upright position to a supine position can result in an impedance signal that takes, e.g., on the order of two hours to reach steady state. Impedance signal measurements can be obtained by measuring the impedance signal between two or more electrodes of the implantable device. As will be appreciated by one of ordinary skill in the art in light of the teachings contained herein, myriad different strategies for measuring the impedance signal can be applied. For example, the impedance signal can be continuously measured once the change in posture is detected. Alternatively, the impedance signal can be measured after some time has passed, for example after an hour and a half has passed with the patient maintaining the second posture. Still further, measuring can begin sporadically once the change in posture is detected, and grow more frequent as a lapse in time approaches an anticipated or previously measured assumption of steady state.

An amount of time required for the impedance signal indicative of left atrial pressure and/or intra-thoracic fluid volume to achieve steady state can be determined based on the collective impedance signal measurements. Further, the steady state impedance signal amplitude can be determined based on the collective impedance signal measurements. At step 1006, pulmonary edema or a worsening of a condition of pulmonary edema can be monitored based on the determined amount of time that it takes the impedance signal to achieve steady state. Further, the steady state impedance signal amplitude can be compared with previous measurements as a basis for monitoring pulmonary edema and worsening of a condition of pulmonary edema.

At step 1008, a degree of the pulmonary edema of the patient, or a change therein is identified as potentially problematic when one or both of an amount of time to achieve steady state exceeds a threshold, or a change in steady state impedance signal amplitude exceeds a threshold. For example, when moving from upright to supine, an increase in time to reach steady state may be indicative of a patient's health improving, while when moving from supine to upright, an increase in time to reach steady state may be indicative of a patient's health worsening. As above, impedance signal measurements can be obtained simultaneously or staggered in time along multiple different vectors between two or more electrodes.

At step 1010, a response can be triggered if appropriate, when the degree of the pulmonary edema of the patient, or the change there is identified as potentially problematic. If monitoring for pulmonary edema is performed by circuitry of the implantable device, the implantable device can trigger a response by applying corrective treatment or providing a warning signal to the patient or the patient's physician by sending the warning signal and/or appropriate data to an external device. As explained in detail above, a telemetry circuit 264 of the implantable device 100 can communicate a warning signal and/or appropriate data via a communication link 266 to the external device 254, and the external device 254 can communicate a warning signal to the patient using a visual warning on a display screen 552 or an audible warning emitted from a speaker 556. One or ordinary skill in the art will appreciate, upon reflecting on the teaching contained herein, the myriad different ways in which a patient and/or physician can be alerted to an abnormality by an implantable device capable of establishing a communication link via a telemetry circuit.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 7, 8 and 10. Further, it is possible to change the order of some of the steps shown in FIGS. 7, 8 and 10, without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method to monitor left atrial pressure (LAP) of a patient comprising:
   (a) storing data indicative of an impedance signal for at least a first specified period of time, obtained using implanted electrodes, and a corresponding posture of the patient, as determined using an implanted posture sensor;
   (b) identifying, based on the stored data, one or more snapshots of the impedance signal where the patient is in a predetermined posture and where prior to each snapshot the patient substantially maintained the predetermined posture for at least a second specified period of time, and during the snapshot the patient maintained the predetermined posture for at least a third specified period of time;

(c) calculating, for each of the identified one or more snapshots of the impedance signal, a separate zLAP value indicative of the patient's left atrial pressure (LAP) while the patient is in the predetermined posture;

(d) identifying an undesirably abnormal change in the patient's left atrial pressure (LAP) in response to at least one of
  (d.1) detecting a change in the calculated zLAP values by a predefined amount, or
  (d.2) detecting a trend in the calculated zLAP values that are symptomatic of organ damage and/or failure; and (e) one or both of triggering an alert or adjusting therapy administered to the patient in response to identifying the abnormality.

2. The method of claim 1, further comprising, after step (b), writing over or otherwise erasing the stored data, indicative of the impedance signal and the corresponding posture of the patient, not associated with the identified snapshots.

3. The method of claim 1, wherein after the first specified period of time steps (a), (b) and (c) are repeated for further periods of time of the same or different length until actively interrupted.

4. The method of claim 1, wherein steps (a), (b), (c), (d) and (e) are performed by an implanted device including and/or connected to the implanted electrodes; and wherein when an alert is triggered, the method further comprises:
  (f) transmitting the alert from the implantable device to a non-implanted device; and
  (g) displaying a visual warning and/or issuing an audible warning by way of the non-implanted device in response to the alert.

5. The method of claim 1, wherein steps (a), (b), (c), (d) and (e) are performed by an implanted system including and/or connected to the implanted electrodes; and wherein when therapy administered to the patient is adjusted, the method comprises:
  adjusting medication based on a physician pre-determined formula; and
  displaying a visual indication of the medication adjustment to the patient.

6. The method of claim 1, wherein steps (a), (b), (c), (d) and (e) are performed by an implanted system including and/or connected to the implanted electrodes; and wherein when therapy administered to the patient is adjusted, the method comprises adjusting electrical therapy administered by an implantable cardioverter-defibrillator (ICD) or cardiac resynchronization therapy defibrillator (CRT-D).

7. The method of claim 1, wherein a portion of the impedance signal is not disqualified from being identified as a snapshot if during the second period of time the posture of the patient changes from the predetermined posture to another identified posture for less than a specified brief time period and then returns from the other identified posture to the predetermined posture.

8. A system to monitor left atrial pressure (LAP) of a patient, comprising:
  an implantable posture sensor adapted to determine a posture of the patient; and
  memory adapted to store data indicative of an impedance signal for at least a first specified period of time, obtained using implanted electrodes, and a corresponding posture of the patient, as determined using the implanted posture sensor;
  a monitor adapted to
    identify, based on the stored data, one or more snapshots of the impedance signal where the patient is in a predetermined posture and where prior to each snapshot the patient substantially maintained a predetermined posture for at least a second specified period of time, and during the snapshot the patient maintained the predetermined posture for at least a third specified period of time;
    calculate, for each of the identified one or more snapshots of the impedance signal, a separate zLAP value indicative of the patient's left atrial pressure (LAP) while the patient is in the predetermined posture;
    identify an undesirably abnormal change in the patient's left atrial pressure (LAP) in response to at least one of
      a change in the calculated zLAP values by a predefined amount, or
      a trend in the calculated zLAP values that are symptomatic of organ damage and/or failure; and
    one or both of trigger an alert or adjust therapy administered to the patient in response to identifying the abnormality.

9. The system of claim 8, wherein a portion of the impedance signal is not disqualified from being identified as a snapshot if during the second period of time the posture of the patient changes from the predetermined posture to another identified posture for less than a specified brief time period and then returns from the other identified posture to the predetermined posture.

10. A method to monitor left atrial pressure (LAP) of a patient, comprising:
  (a) monitoring posture of the patient using a posture sensor implanted within the patient; and
  (b) using portions of an impedance signal, obtained using implanted electrodes, to calculates zLAP values indicative of the patient's left atrial pressure (LAP),
    wherein each said portion of the impedance signal, being used to calculate a said zLAP value, corresponds to a period after which the patient has substantially maintained a predetermined posture for at least a predetermined period of time, and during which the patient has remained in the predetermined posture;
  (c) identifying an undesirably abnormal change in the patient's left atrial pressure (LAP) based on the calculated zLAP values; and
  (d) one or both of triggering an alert or adjusting therapy administered to the patient in response to identifying the abnormality.

11. The method of claim 10,
wherein the impedance signal is obtained continuously;
further comprising, prior to step (b), storing only the portions of the impedance signal corresponding to a period after which the patient has maintained the predetermined posture for at least the predetermined period of time, and during which the patient has remained in the predetermined posture; and
wherein step (b) comprises using the stored portions of the impedance signal to calculates the zLAP values indicative of the patient's left atrial pressure (LAP).

12. The method of claim 10, further comprising, prior to step (b):
  identifying periods when the patient has maintained the predetermined posture for at least the predetermined period of time; and obtaining the impedance signal in response to identifying that the patient has maintained the predetermined posture for at least the predetermined period of time, and during which the patient remains in the predetermined posture.

13. The method of claim 10, wherein steps (a), (b) (c) and (d) are performed by an implanted system including the implanted posture sensor and the implanted electrodes; and wherein when an alert is triggered, the method further comprises:
   (e) transmitting the alert from the implanted system to a non-implanted system; and
   (f) displaying a visual warning and/or issuing an audible warning by way of the non-implanted system in response to the alert.

14. The method of claim 10, wherein steps (a), (b) (c) and (d) are performed by an implanted system including the implanted posture sensor and implanted electrodes; and wherein when therapy administered to the patient is adjusted, the method comprises:
   adjusting medication based on a physician pre-determined formula; and
   displaying a visual indication of the medication adjustment to the patient.

15. The method of claim 10, wherein steps (a), (b) (c) and (d) are performed by an implanted system including the implanted posture sensor and implanted electrodes; and wherein when therapy administered to the patient is adjusted, the method comprises adjusting electrical therapy administered by an implantable cardioverter-defibrillator (ICD) or cardiac resynchronization therapy defibrillator (CRT-D).

16. The method of claim 10, wherein a said portion of the impedance signal is not disqualified from being used to monitor the left atrial pressure (LAP) of the patient if during the predetermined period of time the posture of the patient changes from the predetermined posture to another identified posture for less than a specified brief time period and then returns from the other identified posture to the predetermined posture.

17. A system to monitor left atrial pressure (LAP) of a patient, comprising:
   an implantable posture sensor adapted to determine a posture of the patient; and
   a monitor adapted to
      use portions of an impedance signal, obtained using implanted electrodes, to calculates zLAP values indicative of the patient's left atrial pressure (LAP), wherein each said portion of the impedance signal, used to calculate a said zLAP value, corresponds to a period after which the patient has substantially maintained a predetermined posture for at least a predetermined period of time, and during which the patient has remained in the predetermined posture;
      identify an undesirably abnormal change in the patient's left atrial pressure (LAP) based on the calculated zLAP values; and
      one or both of trigger an alert or adjust therapy administered to the patient in response to identifying the abnormality.

18. The system of claim 17, wherein a said portion of the impedance signal is not disqualified from being used to monitor the left atrial pressure (LAP) of the patient if during the predetermined period of time the posture of the patient changes from the predetermined posture to another identified posture for less than a specified brief time period and then returns from the other identified posture to the predetermined posture.

* * * * *